United States Patent
Covey et al.

(10) Patent No.: US 9,835,588 B2
(45) Date of Patent: Dec. 5, 2017

(54) JET INJECTOR INLET FOR A DIFFERENTIAL MOBILITY SPECTROMETER

(71) Applicant: DH Technologies Development PTE Ltd., Singapore (SG)

(72) Inventors: Thomas R. Covey, Richmond Hill (CA); Bradley Schneider, Bradford (CA); Erkinjon Nazarov, Tampa, FL (US)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/107,487

(22) PCT Filed: Nov. 18, 2014

(86) PCT No.: PCT/IB2014/002517
§ 371 (c)(1),
(2) Date: Jun. 23, 2016

(87) PCT Pub. No.: WO2015/101817
PCT Pub. Date: Jul. 9, 2015

(65) Prior Publication Data
US 2016/0334369 A1 Nov. 17, 2016

Related U.S. Application Data

(60) Provisional application No. 61/935,741, filed on Feb. 4, 2014, provisional application No. 61/922,275, filed on Dec. 31, 2013.

(51) Int. Cl.
*H01J 49/04* (2006.01)
*G01N 27/62* (2006.01)
*H01J 49/00* (2006.01)

(52) U.S. Cl.
CPC ........ *G01N 27/624* (2013.01); *H01J 49/0031* (2013.01)

(58) Field of Classification Search
CPC ................ G01N 27/624; H01J 49/0027; H01J 49/0031; H01J 49/04; H01J 49/26; H01J 49/34; H01J 49/40; H01J 49/42
See application file for complete search history.

(56) References Cited

U.S. PATENT DOCUMENTS 4,234,791 A 11/1980 Enke et al.
7,858,927 B2 12/2010 Thomson
(Continued)

FOREIGN PATENT DOCUMENTS

CN 1342900 A 4/2002
CN 101356433 A 1/2009
(Continued)

OTHER PUBLICATIONS

International Search Report and Written Opinion for PCT/IB2014/002517 dated Feb. 27, 2015.

*Primary Examiner* — David E Smith

(57) ABSTRACT

A method and apparatus for performing differential mobility spectrometer (DMS) which includes decreasing the amount of time that ions spend inside fringing fields generated by the DMS. The apparatus includes an entrance electrode plate sealingly engaged to the entrance of the DMS, and is electrically separated from the parallel plate electrodes of the DMS, the entrance electrode plate has an aperture for allowing the traversal of ions into the DMS; wherein the cross-sectional area of the aperture is less than the cross-sectional area of the ion path, the ion path being located between the two parallel plate electrodes of the DMS. The entrance electrode plate may also have a focusing potential applied to it for focusing of ions.

19 Claims, 19 Drawing Sheets

(56) References Cited

U.S. PATENT DOCUMENTS

| | | |
|---|---|---|
| 2002/0113207 A1 | 8/2002 | Lee et al. |
| 2010/0288919 A1* | 11/2010 | Sheehan ............... H01J 49/067 250/282 |
| 2011/0049356 A1* | 3/2011 | Fernandez De La Mora .................... H01J 49/062 250/283 |
| 2012/0056085 A1* | 3/2012 | Giles .................... G01N 27/624 250/282 |
| 2013/0092834 A1 | 4/2013 | Covey et al. |
| 2013/0264493 A1 | 10/2013 | Covey et al. |
| 2015/0340218 A1* | 11/2015 | Papanastasiou .... H01J 49/0495 250/289 |

FOREIGN PATENT DOCUMENTS

| | | |
|---|---|---|
| CN | 102918525 A | 2/2013 |
| EP | 1521290 A1 | 4/2005 |
| JP | 2010508535 A | 3/2010 |
| WO | 2011094529 A2 | 8/2011 |

\* cited by examiner

JET INJECTOR INLET FOR A DIFFERENTIAL MOBILITY SPECTROMETER

RELATED APPLICATIONS

This application claims the benefit of priority from U.S. Provisional Application Ser. No. 61/922,275, filed on Dec. 31, 2013 and 61/935,741, filed on Feb. 4, 2014, the entire contents of both which are hereby incorporated by reference.

FIELD

The teachings herein are directed to apparatus and methods of introducing ions into a differential mobility spectrometer

BACKGROUND

Ion Mobility based analysis methods separate and analyze ions under elevated pressure conditions (compared to mass spectrometers), based upon differences in the coefficient of mobility in gases. A Differential Mobility Spectrometer (DMS), like a traditional time-of flight ion mobility spectrometer (IMS), separates and analyzes ions based on the mobility characteristics of the ions, but provides orthogonal ion characterization. In IMS ion separation occurs on the basis of ion species cross section, in DMS ion separation occurs on the basis of the alpha parameter, which is related to the differences in the ion mobility coefficient in varying strengths of electric field. Ions are pulsed into an IMS and pass through a drift tube while being subjected to a constant electric field. As they pass through the drift region, ions may interact with drift gas molecules. These interactions are specific for each ion species of a sample, and depend from cross section of analyzed ion species leading to an ion separation based on more than just mass/charge ratio. Due to differences in collision cross sections different ion species have different drift velocity toward the detector plate, yielding different arrival (or drift) times.

In contrast, in the collision-free vacuum conditions of a Time of Flight Mass Spectrometer (ToF-MS), the ion's flight time through the MS flight tube is determined solely by the ion's mass-to-charge ratio (m/z).

A DMS is similar to an IMS in that the ions are separated in a drift gas at ambient pressure conditions. However, unlike an IMS, the DMS uses an asymmetric electric field waveform that is applied between at least two parallel electrodes through which the ions pass, in a continuous manner, swept along in the transport gas flow stream. Ion separation occurs under the effect of a strong asymmetric waveform RF electric field oriented perpendicular to the direction of the transport gas flow stream. The electric field waveform typically has a short time duration at a high field portion of the waveform and then a longer time at a low field duration at an opposite polarity. The duration of the high field and low field portions are applied such that the net voltage (average voltage for one full period) being applied to the DMS filter electrodes is zero. Under these conditions, ions with different field dependent mobility coefficients have different trajectories due to their alpha parameters.

In some circumstances, a DMS has been interfaced with a mass spectrometer (MS) to provide an orthogonal separation method to the MS. This combination which includes two orthogonal methods takes advantage of the atmospheric pressure, gas phase, and continuous ion separation capabilities of the DMS and enhanced analytical power of the DMS-MS system.

By interfacing a DMS with an MS, numerous areas of sample analysis, including proteomics, peptide/protein conformation, pharmacokinetic, and metabolism analysis have been enhanced. In addition to pharmaceutical and biotech applications, DMS-based analyzers have been used for trace level explosives detection and petroleum monitoring.

The resolution of a DMS device improves with the addition of a counter-current gas flow prior to the DMS mobility cell. Such a configuration is exemplified in FIG. 1. A curtain gas is established by placing a curtain plate prior to the inlet of the DMS and applying a DC potential (typically 500-1500 V) to propel ions across the gap between the curtain plate aperture and the DMS inlet. In addition this approach has been demonstrated to help provide effective ion desolvation prior to the mobility analyzer.

It has been found that ion losses mostly occur during the ion introduction in the DMS analytical gap. This is a result from the presence of fringing electric fields which result from the presence of superimposed separating (RF) and compensation (DC) electric fields in the analytical gap of the DMS. Additionally, it has also been found that the efficiency of ion introduction into a DMS cell can be affected by the absolute values of the applied separation and compensation voltages, which lead to changing the effective trajectories of ions that are distinguished by coefficient mobility, polarity, and electric field dependence (alpha parameters). In some devices, for example, in systems with narrow analytical gaps, this manifests itself as significantly reduced signal measured when used in transparent mode (where no asymmetric or compensation voltage is applied) and introduces discrimination in ion transmission between ions with high and low mobility coefficients.

SUMMARY

In various embodiments, the presence of fringing electric fields on the entrance or/and exit of a DMS inevitably decreases the coefficient of ion transmission through the analytical gap. This unwanted effect depends upon many parameters of DMS sensors: physical size of analytical gap, linear velocity of ions through gap (transport gas flow rate), geometry of electrodes which are used for ion funneling, and mobility of analyzed ion species.

In various embodiments, we have found that a decrease in ion losses in areas of fringing electric field regions can be achieved by reducing the residence time for ions within the detrimental region of a DMS. We suggest two ways to enhance ion transmission through the analytical gap: a) first is via the use of fast injection of ions into the analytical gap by providing a gas beam jet which promptly injects ions into the inlet of the DMS cell and/or b) Pre-focusing ions in the area before the entrance (in areas where the fringing electric field is active) and focus them towards the central axis of the analytical gap. In this embodiment ion introduction occurs due to the harmonic superimposed effects of an additional focusing RF electric field, transport gas flow and prompt jet injection of ions into the analytical gap. The gas beam or jet is used to overcome the detrimental fields present at the inlet so that ions are efficiently injected into the DMS cell. Ion focusing squeezes the ion beam to the axis of the analytical gap where the effects of detrimental fringing electric fields are reduced. In some embodiments, the effects of the detrimental fringing fields can be minimized and even removed from the inlet of a DMS cell by providing a shielding electrode prior to the mobility analyzer which is simultaneously used for forming the appropriate (by adjusting its aperture) jet. The additional electrode can be sealed into the DMS assembly simultaneously providing shielding and beam/jet formation. The gas beam or jet can be directed into the central axis of the DMS cell to ensure that targeted ion species are substantially removed from insulating surfaces at the front of the DMS slot.

In various embodiments, a differential mobility apparatus is provided which comprises a housing having an entrance and an exit, at least two parallel plate electrodes disposed within said housing separated from one another by a fixed distance, the volume between the two electrodes defining an ion path through which ions flow from the entrance to the exit, the ion path having a cross-sectional area normal to the direction of ion flow, a voltage source for providing RF and DC voltages to at least one of the parallel plate electrodes to generate an electric field, the electrical field for passing though selected ions species based on mobility characteristics, a drift gas supply for supplying a gas that flows through the entrance to the exit; and at least one entrance electrode plate sealingly engaged to the entrance, and electrically separated from the parallel plate-electrodes, the at least one entrance electrode plate having an aperture for allowing the traversal of ions and the gas into the housing, wherein the cross-sectional area of the aperture is less than the cross-sectional area of the ion path.

In various embodiments, a method of analyzing ions in a differential mobility device is provided, the device having two parallel plate electrodes that generate an electric field, the method comprising introducing ions into a drift gas and directing said drift gas towards an inlet of the differential mobility device, accelerating the drift gas as it enters the differential mobility device and decelerating the drift gas once the drift gas has entered the differential mobility device, performing a differential mobility separation on the ions using the differential mobility device and detecting the ions.

In various embodiments, a differential mobility filter apparatus system is provided which comprising an ionization source for generating ions, a curtain chamber defined by at least one curtain plate, the curtain plate containing a curtain plate aperture through which the ions flow, a curtain gas supply in fluid communication with the curtain chamber, a housing disposed within the curtain chamber, the housing having an opening and an exit, the volume between the opening and exit defining an ion path, the ion path being generally in line with the curtain plate aperture and the opening being in fluid communication with the curtain chamber, at least two parallel plate electrodes disposed within the housing and being oriented opposite and separated by a fixed distance from one another on either side of the ion path, a voltage source and controller for providing RF and DC voltages to at least one of the parallel plate electrodes to generate an electric field, the electrical field for passing though selected portions of ions based on mobility characteristics, at least one entrance electrode plate sealingly engaged to the opening, and electrically separated from the parallel plate electrodes, the at least one entrance electrode plate having an aperture for allowing the traversal of ions and the gas into the housing, wherein the cross-sectional area of the aperture is less than the cross-sectional area of the ion path.

In various embodiments, the differential mobility apparatus can operate in transparent mode.

In various embodiments, the one entrance electrode plate is removable.

In various embodiments, the aperture is contained within an iris diaphragm and is adjustable to vary the flow of gas through the entrance.

In various embodiments, the at least one entrance electrode plate is electrically separated from the parallel plate electrodes and wherein a controller and generator are connected to the at least one entrance electrode plate for applying an RF focusing potential and/or a DC potential.

In various embodiments, the differential mobility apparatus further comprises a vacuum source positioned downstream from said parallel plate electrodes.

In various embodiments, the housing is surrounded by a curtain plate that defines a curtain chamber and the curtain chamber is in fluid communication with a curtain gas supply that provides a curtain gas to the curtain chamber wherein the curtain gas in the curtain chamber becomes the drift gas supply, the curtain chamber having at least one aperture which allows ions to flow therethrough.

In various embodiments, the orifice is either circular or slit shaped.

In various embodiments, the two electrode plates are sealingly engaged to the entrance and each of the two electrode plates are electrically insulated from the parallel plate electrodes and each of the two electrode plates is electrically insulated from each other, each of the two electrode plates being connected to an RF source and controller for generating an RF focusing field.

In various embodiments, the accelerating of the drift gas comprises passing the drift gas through an aperture that is defined within one or more electrode plates that are sealingly engaged to the face of the parallel plates and the decelerating of the drift gas is performed by the expansion of the drift gas upon exiting the aperture, wherein the cross section of the aperture is less than the cross section of the inlet of the differential mobility device.

In various embodiments, the accelerating of the drift gas also comprises applying suction downstream from the two parallel plate electrodes, the suction being provided by a vacuum source.

In various embodiments, the differential mobility device operates with only DC voltages.

In various embodiments, the differential mobility device is surrounded by a curtain plate which defines a curtain chamber and the curtain chamber is in fluid communication with a curtain gas supply that provides a curtain gas to the curtain chamber wherein the curtain gas becomes the drift gas that flows into the differential mobility device, and the curtain plate has at least one aperture that allows ions to flow therethrough.

In various embodiments, an RF focusing potential is applied to the one or more electrode plates for focusing of the ions.

In various embodiments, the entrance electrode place comprises an iris diaphragm, the iris diaphragm defining the aperture and being adjustable to vary the flow of gas through the opening.

In various embodiments, the cross sectional area of the ion path is defined as the distance between the parallel plate electrodes times the width of the parallel plate electrodes.

In various embodiments, the apparatus operates with only DC voltages.

In various embodiments, an RF controller and generator is connected to the entrance electrode plate for applying an RF focusing potential.

In various embodiments, the apparatus further comprises a vacuum source connected downstream from the two parallel plate electrodes, said vacuum source for accelerating curtain gas flow into and through the housing.

In various embodiments, the apparatus further comprises an additional device operably coupled to the exit, wherein the additional device is selected from a mass spectrometer, a Raman spectrometer and another DMS device.

In various embodiments, two entrance electrode plate are sealingly engaged to the entrance, the two entrance electrode plates being electrically insulated from each other, the first of the entrance electrode plate defining a first cut out portion and the second of the entrance electrode plate defining a second cut out portion, the first and second cut out portions co-operating to form the aperture.

In various embodiments, an RF focusing potential is applied from the first entrance electrode plate to the second entrance electrode plate.

BRIEF DESCRIPTION OF THE DRAWINGS

FIG. 12 depicts normalized ionograms for a number of analytes with a 3.5 mm (optimized) injector compared to a conventional DMS device. Compensation Voltages in both cases are similar.

DETAILED DESCRIPTION OF VARIOUS EMBODIMENTS

Figure 1:
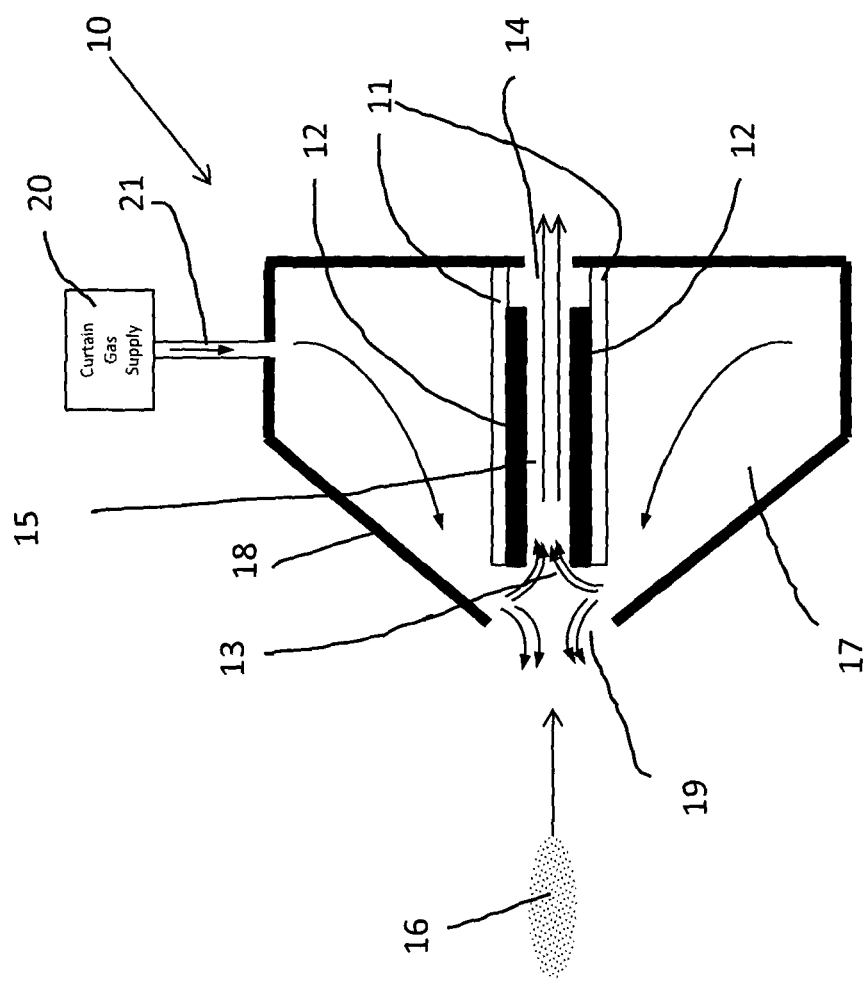
FIG. 1 depicts a layout of a typical DMS device.

FIG. 1 depicts the configuration of a typical DMS device 10. A housing 11 surrounds two parallel electrodes 12 in which an asymmetric voltage and compensation voltage can be applied. The space between the two electrodes defines an analytical gap having a volume. The housing 11 has an entrance 13 into which ions and gas can flow and an exit 14. The area between the entrance and exit defines a path 15 through which ions flow. Ions 16 entering the housing 11, pass between the two parallel electrodes 12 where they are subjected to asymmetric and compensation fields that can separate ions having differing ion mobility properties.

As would be understood, the electrodes 12 are connected to a suitable power source and controller that allows the generation of RF and DC fields through the electrodes 12. While the electrodes 12 are described herein using the same identifier, it would be appreciated that the electrodes can be configured so that separate RF and/or DC potentials can be transmitted separately to each of the two electrodes so that the pair of electrodes operate individually as distinct electrodes.

A curtain chamber 17 surrounds the housing 11 which is defined by a curtain plate 18. The curtain plate 18 contains an opening directly in line with the entrance of the housing 13. A curtain gas supply 20 is fluidly connected to the curtain chamber 17 by conduit 21 and supplies curtain gas to the curtain chamber 17. The curtain gas fills the curtain chamber and flows out of the opening 19 of the curtain chamber 17 and into the opening 13 of the housing 11. The housing 11 is configured such that curtain gas can only enter and flow past the parallel electrodes 12 by way of the housing opening 13. Curtain gas that enters into the housing 11 becomes a drift gas and flows between the two parallel plate electrodes 12 and leaves the housing 11 through the housing exit 14.

Ions 16 from a suitable ionization source (such as electrospray, chemical, MALDI, etc.) approach the entrance 19 of the curtain chamber 17 where they pass through a counter-current flow from the exiting curtain gas, which assists in drying of the ions. A voltage applied to the curtain plate 18 from a suitable source propels ions 16 across the gap between the curtain plate 18 and the entrance 13 to the housing 11. Upon entering the housing 11, the ions 16 are swept along in the drift gas, and the asymmetric voltages applied to the parallel electrodes 12 cause separation of ions based on ion mobility properties. The ions 16 and drift gas continue to travel down the ion path 15 to the exit 14 where the ions may be detected or subjected to further processes or devices such as mass spectrometry.

Figure 2:
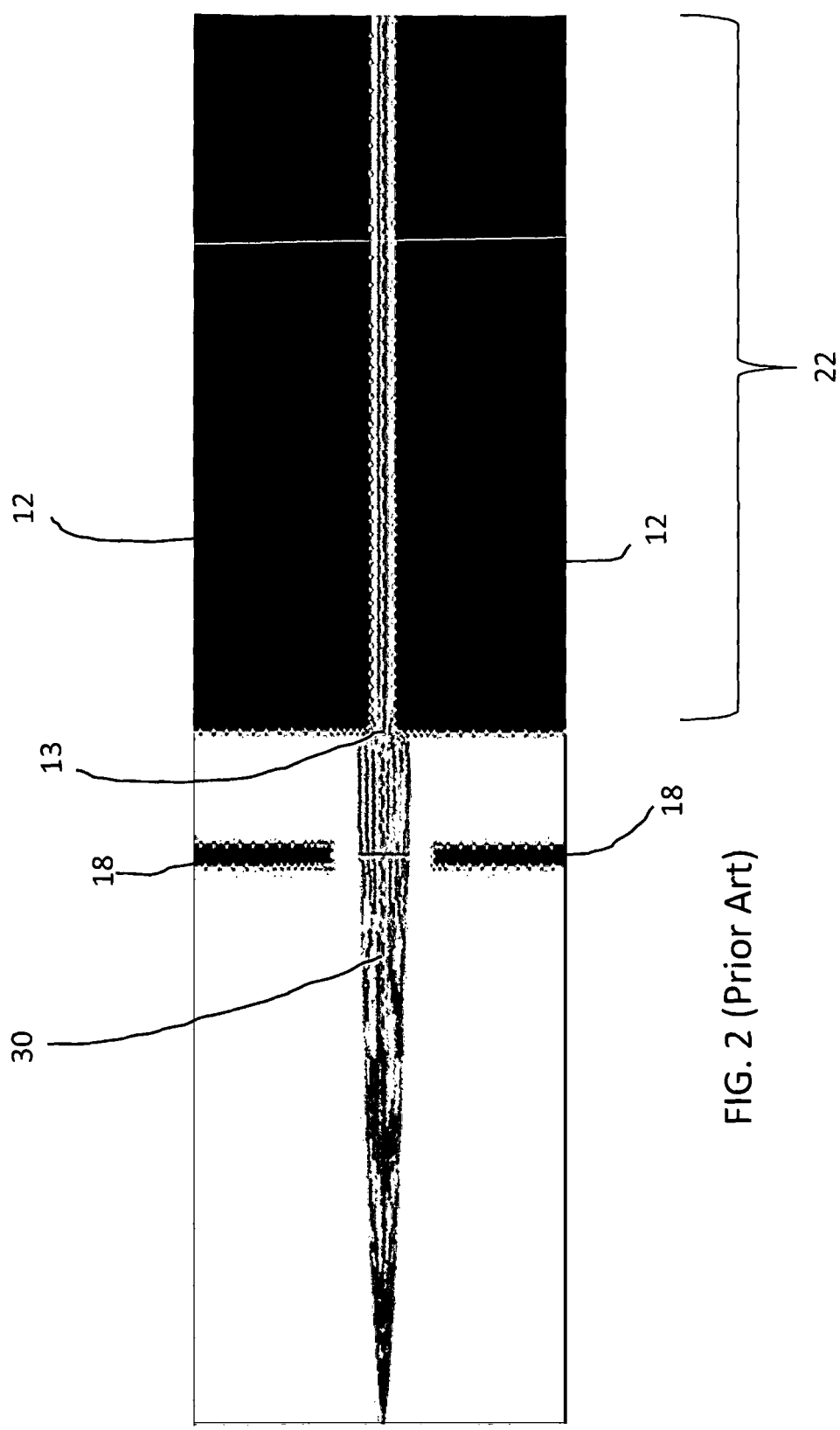
FIG. 2 depicts a view of ion trajectories at the inlet of a conventional DMS device.

FIG. 2 depicts a simplified view of the opening 19 of the curtain plate 18 and the entrance 13 to the housing 11 and ion trajectories 30 through a conventional configuration. The two parallel plate electrodes 12 and the curtain plate boundary 18 are shown along with the tip of an electrospray ion source sprayer that generates streams of ions 16. The ions 16 pass through a curtain plate 18 and finally arrive at the inlet 13 of a DMS cell 22 consisting of the two parallel electrodes 12. The electric field established between the curtain plate 18 (at approximately 500 V) and the DMS inlet 13 is divergent resulting in lower ion transmission into the DMS 22. Specifically only two ion streams of the initial fifteen streams make it into the DMS 22. The remaining streams impinge on the front face of the parallel plate electrodes 12 and are removed.

Figure 3:
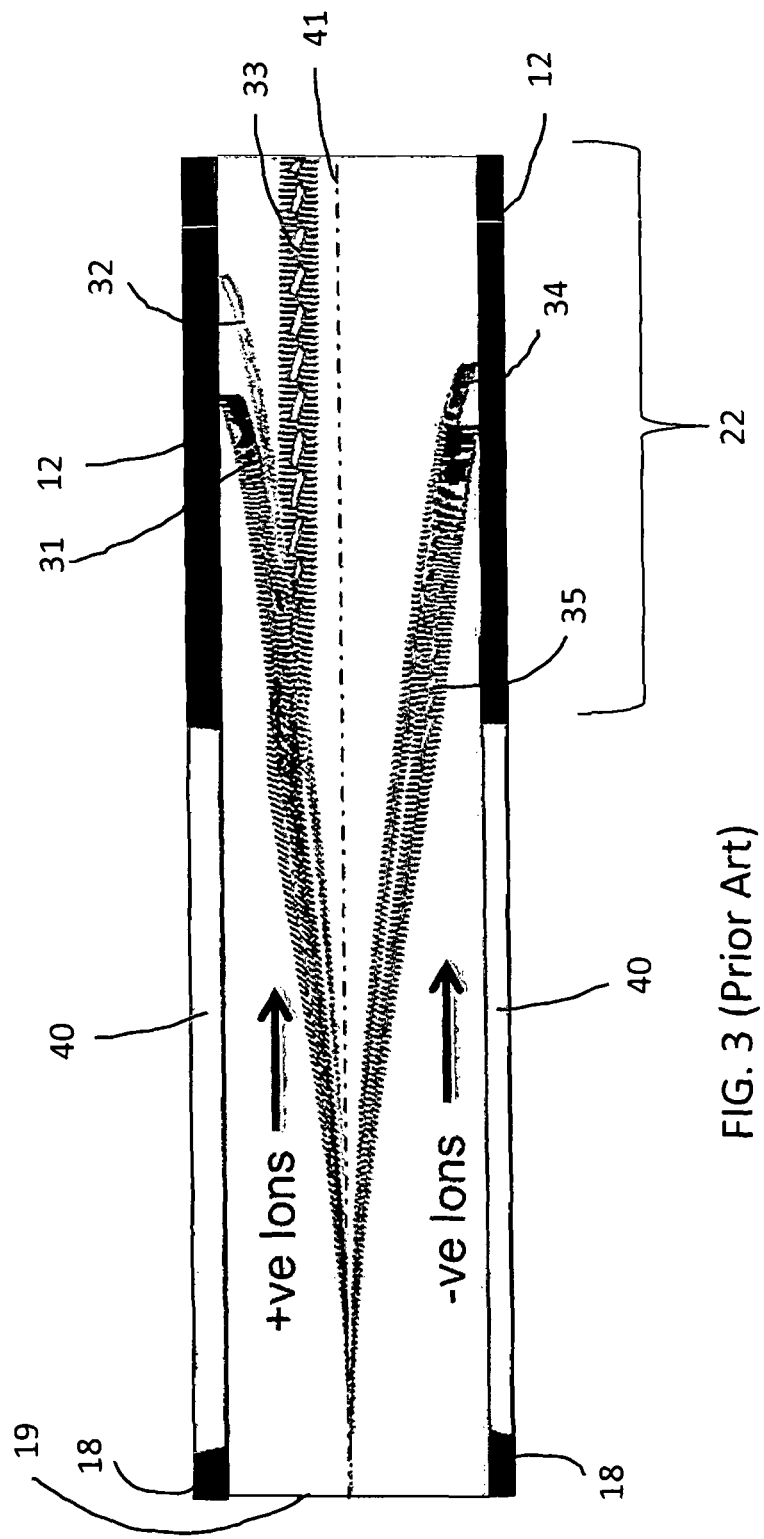
FIG. 3 depicts an alternative view of ion trajectories for different ion species at the inlet of a conventional DMS device.

FIG. 3 shows a more detailed view of the effects on the ion trajectories (31, 32, 33, 34, 35) through the fringing fields as a result of the application of different DC potentials to the two DMS electrodes 12 (i.e. compensation voltage) for five different ions. The trajectories demonstrate the oscillatory nature of ions due to the application of the asymmetric field. The three trajectories (31, 32, 33) above the midline point 41 represent positively charged ions and the two trajectories (34, 35) below the midline 41 point represent negatively charged ions. In this figure, the ions pass through the aperture 19 of the curtain plate 18, and then pass through a region where the walls 40 are otherwise the same width as the curtain plate aperture 19 and act as non-conductive insulators, prior to entering the DMS cell 22 which contains two parallel plate electrodes 12. A positive DC compensation voltage (CoV) is applied to the bottom electrode, and the fringing field resulting from this influences the motion of ions shortly after passing through the curtain plate aperture 19. Positive ions are deflected away from the bottom plate, and negative ions are attracted towards the bottom plate, resulting in segregation of the different polarity ions prior to entering of the DMS cell 22. In addition, the fringing field effects limit the acceptance region for the DMS cell 22 because positive ions located above the center axis 41 of the DMS would more likely be lost on the top electrode and negative ions located below the center axis 41 of the DMS would more likely be lost on the bottom electrode. The ion trajectories have been compromised prior to the entrance of the ions into the DMS cell 22 as a result of the detrimental effects of the fringing fields. Though one of the ion trajectories 33 is able to be recovered to traverse through the DMS cell 22, the initial positioning of the ion as it enters the DMS cell 22 is off centre due to the presence of the fringing fields. If the initial positioning of the ion stream at for example the curtain plate aperture 19 were above the midpoint line 41, this trajectory could also have resulted in an unstable path by contacting the upper electrode. The modeling results of FIG. 3 also demonstrate that the ions are affected by the asymmetric RF voltage shortly after passing through the curtain plate aperture, however, the result is a slight saw-tooth motion to the ions. The DC field from the presence of the compensation voltage has a much more detrimental effect on the ion trajectories than the SV.

Figure 4:
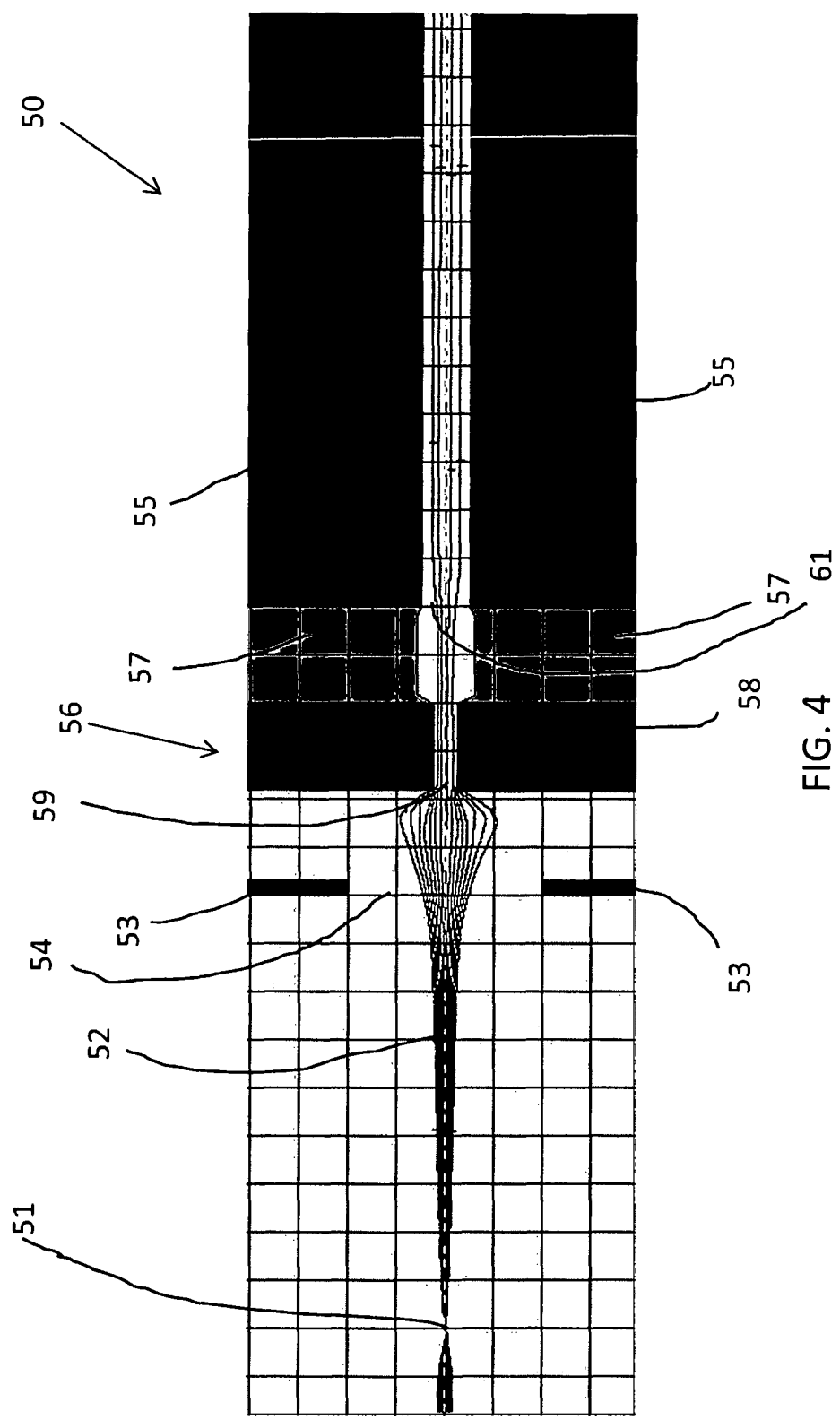
FIG. 4 depicts a view of ion trajectories at the inlet in an embodiment of the present teachings

FIG. 4 depicts an example of a DMS apparatus 50 configuration embodied by the present teachings. Similar to the conventional device depicted in FIG. 2, the DMS device 50 contains an ion source sprayer 51 that generates ion streams 52, a curtain plate 53 containing an aperture 54, and parallel plate electrodes 55 which form the analytical gap of a DMS. The DMS device 50 however contains an additional jet injector electrode 56 positioned between the curtain plate 53 and the parallel plate electrodes 55 at the entrance to the housing. The injector electrode 56 is composed of a single conductive jet injector plate 58 electrically separated and in addition is isolated from the parallel plate electrodes 55, such as for example by an insulating material 57 that prevents the voltages being applied to the parallel plate electrodes 55 from being transmitted to the injector electrode 56. The jet electrode 56 contains orifice 59 which can be a circular, slit shaped or any suitable shape. The orifice 59 is generally in line with the stream of the ions 52, the opening 54 of the curtain plate 53 and the entrance of the DMS cell 61 so that ions passing from the ion sprayer 51, pass through the opening of the curtain plate 54, the orifice of the jet electrode 59 and then the entrance of the DMS cell 61. The jet electrodes 56 can be separated from the DMS parallel electrodes 55 by way of an electrically insulating material 57 and is sealingly engaged to the DMS electrodes 55 preventing the inflow or outflow of gas other than through the orifice opening 61 or from the exit of the DMS cell, downstream from the parallel plate electrodes 55. Alternatively, the insulating material 57 may be replaced partially with a static air gap so long as the jet electrode remains sealingly engaged to the DMS electrodes to prevent the inflow of gas other than through the jet injector orifice 19. The cross sectional area 62 of the orifice 59 in the jet electrodes 56 is smaller than the cross sectional area 63 of the ion path situated between the two parallel plate electrodes 55. The jet injector electrode 56 can be operated at a DC potential similar or different from the DMS cell to optimize transmission into the DMS inlet. It has been surprisingly found that even though the cross sectional area of the orifice 62 in the jet electrodes 56 is lower than the cross sectional area 63 of the ion path between the two parallel plate electrodes 55 and that more ions would be expected to impinge on the surface of the electrode 56, that this configuration results in more ion streams being transmitted into the DMS cell, due to ion funneling. That is, a greater number of the original ion distribution was transmitted through the DMS device. Specifically in this example, four streams of ions are transmitted into the cell. While not wishing to be bound by theory, it is believed that a loss of ions due to this decrease in available orifice transmission capability (by way of reduced cross section) in the jet electrode is more than made up by the increase in velocity of gas and ions travelling through the orifice (due to the decreased cross sectional area at fixed gas flow) which results in a decrease in time in which the ions experience the detrimental effects of the fringing fields. The jet injector DMS configuration also improves ion transfer in the DMS as the stronger (with higher linear velocity) gas flows are used to direct ions more towards the center of the electrode set to improve transmission.

Figure 18:
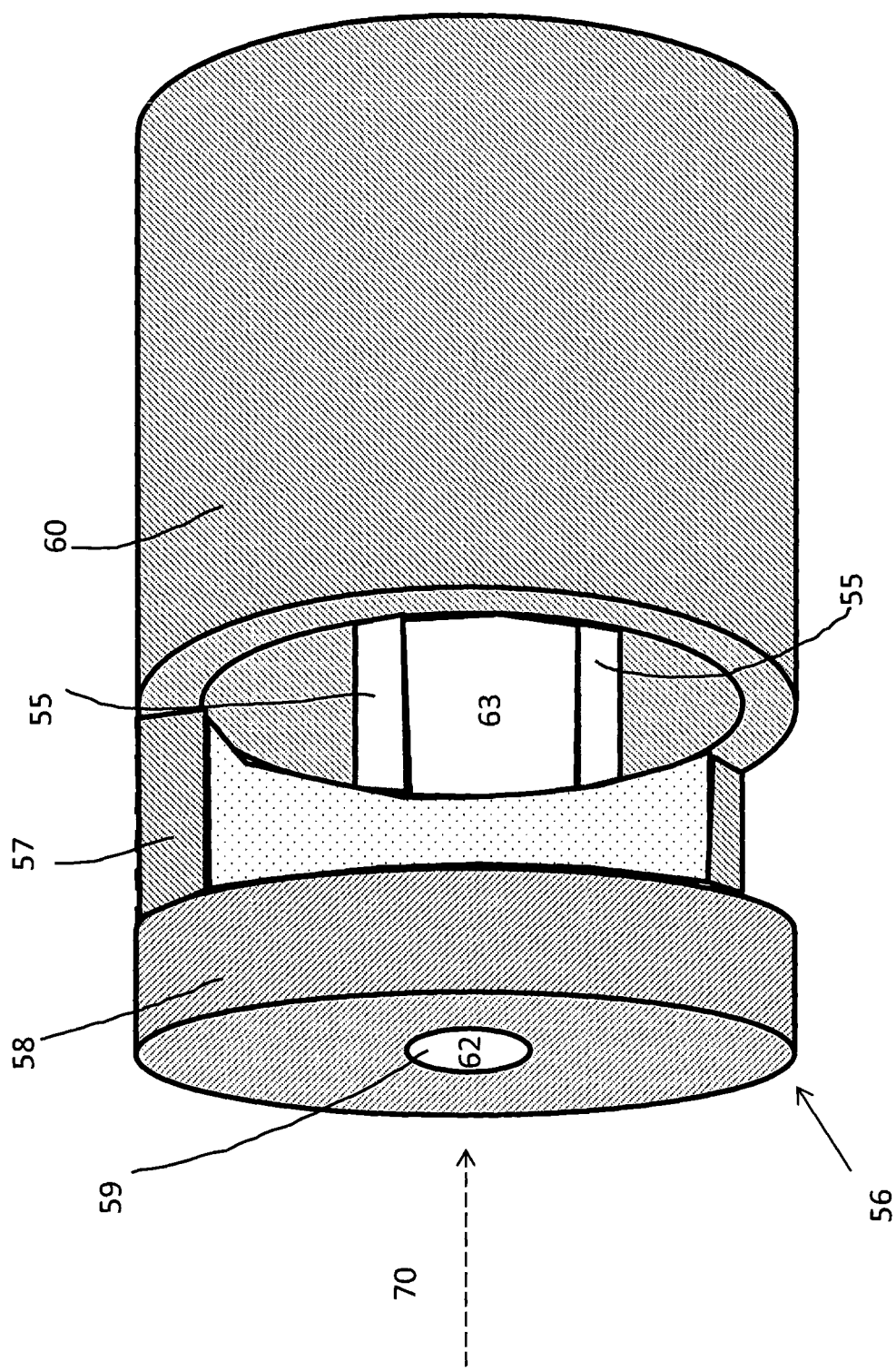
FIG. 18 depicts an embodiment of the present jet assistant teachings
Figure 19:
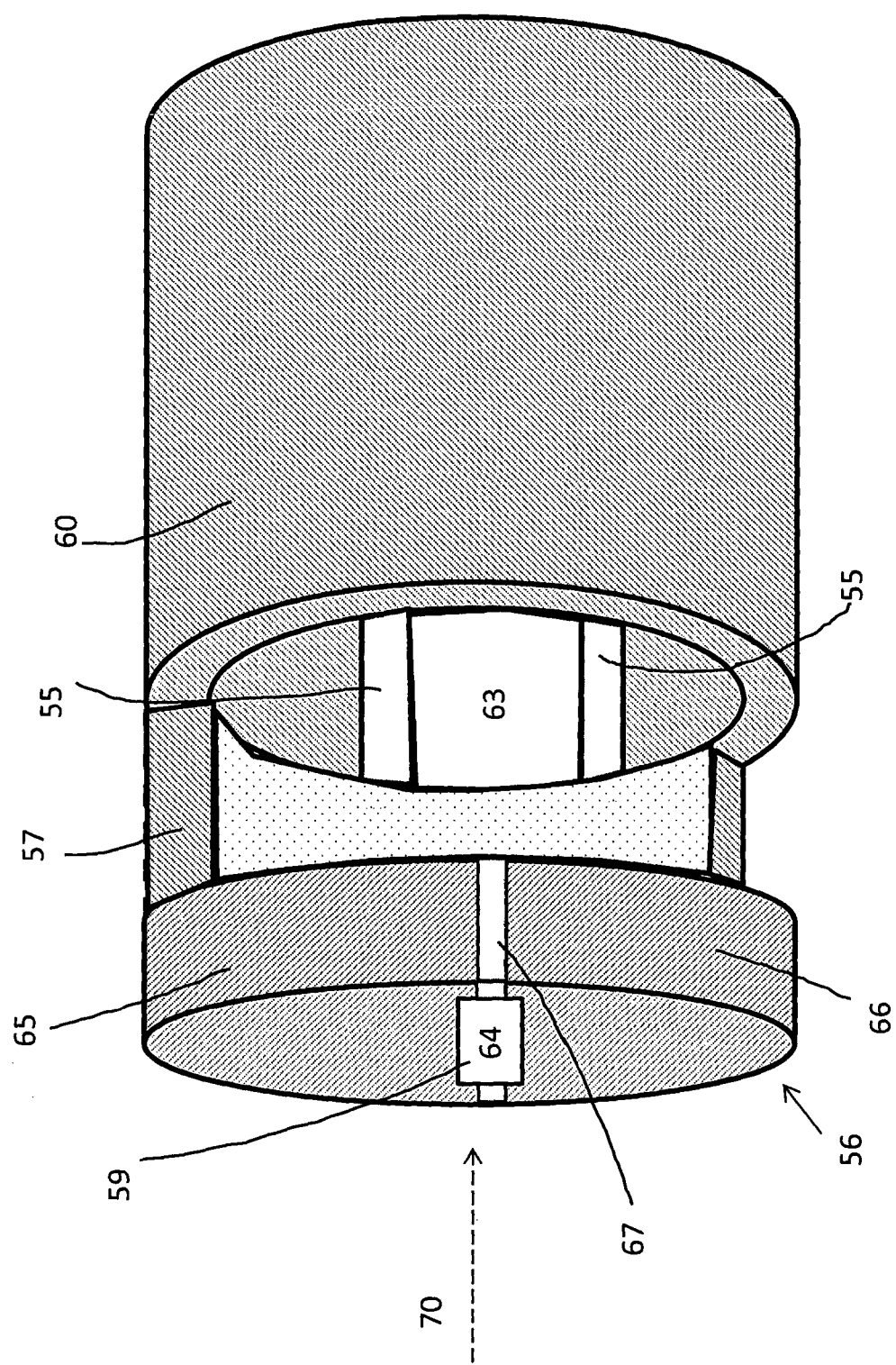
FIG. 19 depicts an alternative embodiment of the present jet assistant teachings

For greater clarification, when referring to the cross sectional area 62 of the jet injector electrode 56 and the cross sectional 63 area of the ion path between the two parallel plate electrodes 55, the areas referred to can be more easily visualized in FIG. 18, wherein a drawing of the jet assistant ions injection system is presented. The cross sectional 62 area of the aperture 59 of the jet injector electrode 56 which consists of the single jet injector plate 58 is smaller than the cross sectional area 63 of the ion path between the two parallel plate electrodes 55. In both cases, the cross sectional areas are the planar areas that are normal to the direction of ion flow 70. The cross sectional area 62 of the aperture 59 of the jet injector electrode 56 is generally circular, whereas the cross sectional area 63 of the ion path is generally rectangular. The two cross sectional areas do not need to be of the same cross sectional shape. The insulating material 57 used to separate the parallel plate electrodes 55 from the jet injector plate 58 has been cut away to allow visualizing of the interior. Another embodiment is described in FIG. 19 which is similar to the embodiment described in FIG. 18 with the exception that the aperture 59 is slit shaped and the jet injector electrode 56 is formed from a top injector plate 65 and a bottom injector plate 66. Each of these two plates are separated from one another by an insulator material 67. In this manner, an RF field can be generated across the two electrodes. The two injector plates (65,66) form the top and bottom portions of the orifice 59 of slit shape and having cross sectional area 64. The top and bottom injector plates both have cut-outs which co-operate together to form the aperture 59. The cross sectional area of the slit 64 is generally of the same shape of the cross sectional area 63 of the ion path. Other aperture configurations may also be utilized.

Figure 5:
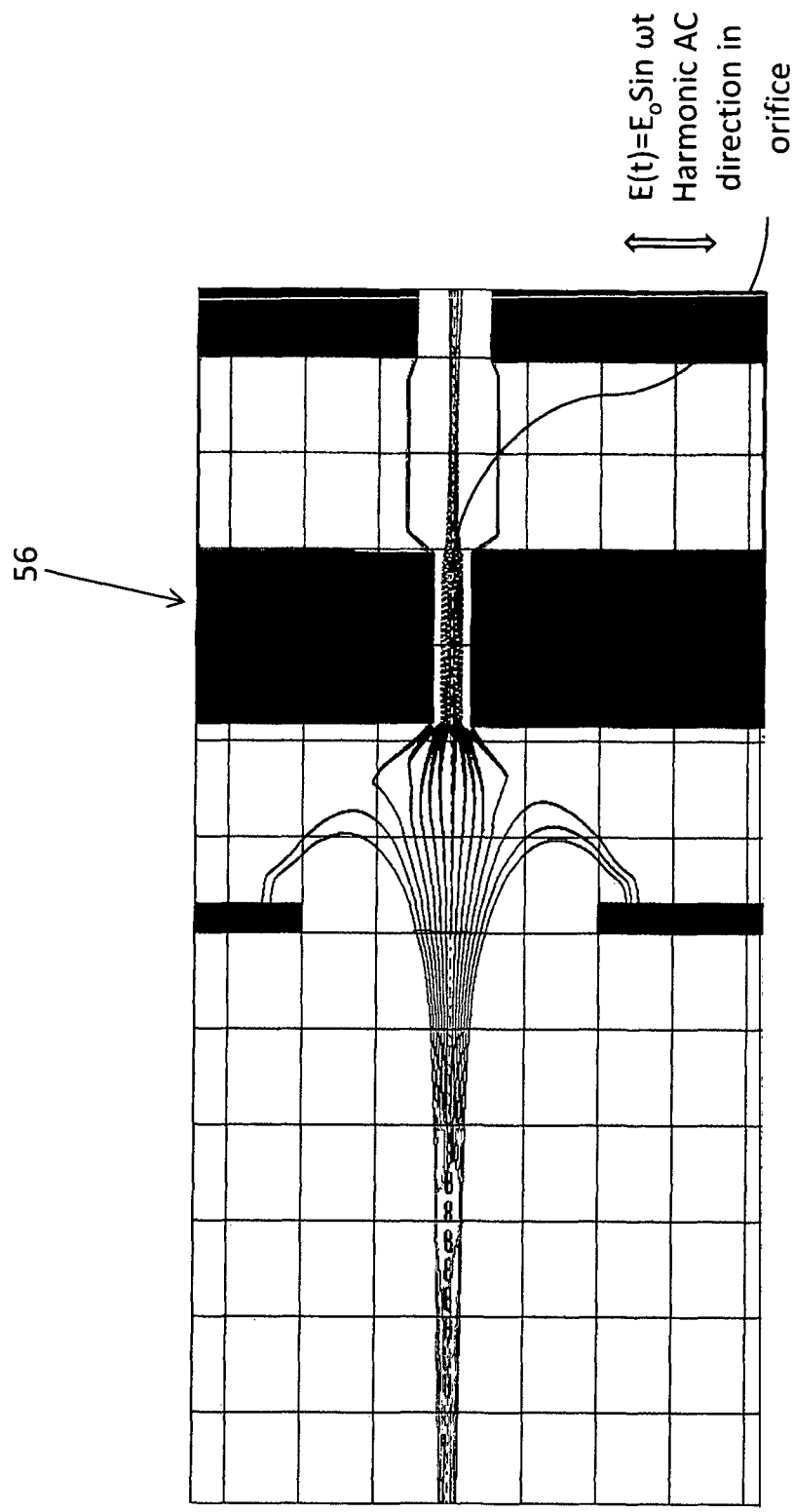
FIG. 5 depicts a view of the ion trajectories at the inlet in an alternative embodiment of the present teachings showing ion funneling/focusing towards the axis of the analytical gap

FIG. 5 depicts another embodiment of the present teachings. We have found that by applying an additional periodic/harmonic RF/AC electric field across the jet forming aperture that the efficiency of ion injection can be increased. This improvement occurs due to the focusing of ions towards the center of the jet aperture due to the superimposed effect of the RF electric field and gas flow. This combination causes the ion beam to squeeze to the center of the orifice at the entrance and exhaust of orifice as depicted in FIG. 5 where the ion beam becomes more narrow upon leaving the jet injector electrode 56 leading up to the entry into the analytical gap.

In this embodiment even more improvements in ion transmission can be achieved by applying a focusing RF potential onto the jet electrode 56, but is otherwise similar to the embodiment described in FIG. 4. As demonstrated in FIG. 5, an even larger number of ions was transmitted (six streams).

The jet injector plate may also be comprised of two separate electrodes that are insulated from one another so as to form a two electrode system. Furthermore, three or more electrodes may be utilized, with two or more the electrodes being insulated from one another.

Subsequent to leaving the parallel plate electrodes 55, ions may be further transported to other devices for manipulation and/or filtering and/or detected. In some embodiments, the curtain chamber has an exit aperture generally in line with the exit of the housing and ion path which allows ions to leave the curtain chamber where they may then be passed onto other devices. Exemplary examples of such devices include a detector, a mass filter, a mass spectrometer, other types of spectrometers such as Raman or IR and other mobility based devices such as another DMS system, a high field asymmetric waveform ion mobility spectrometer and an ion mobility spectrometer device.

Figure 6:
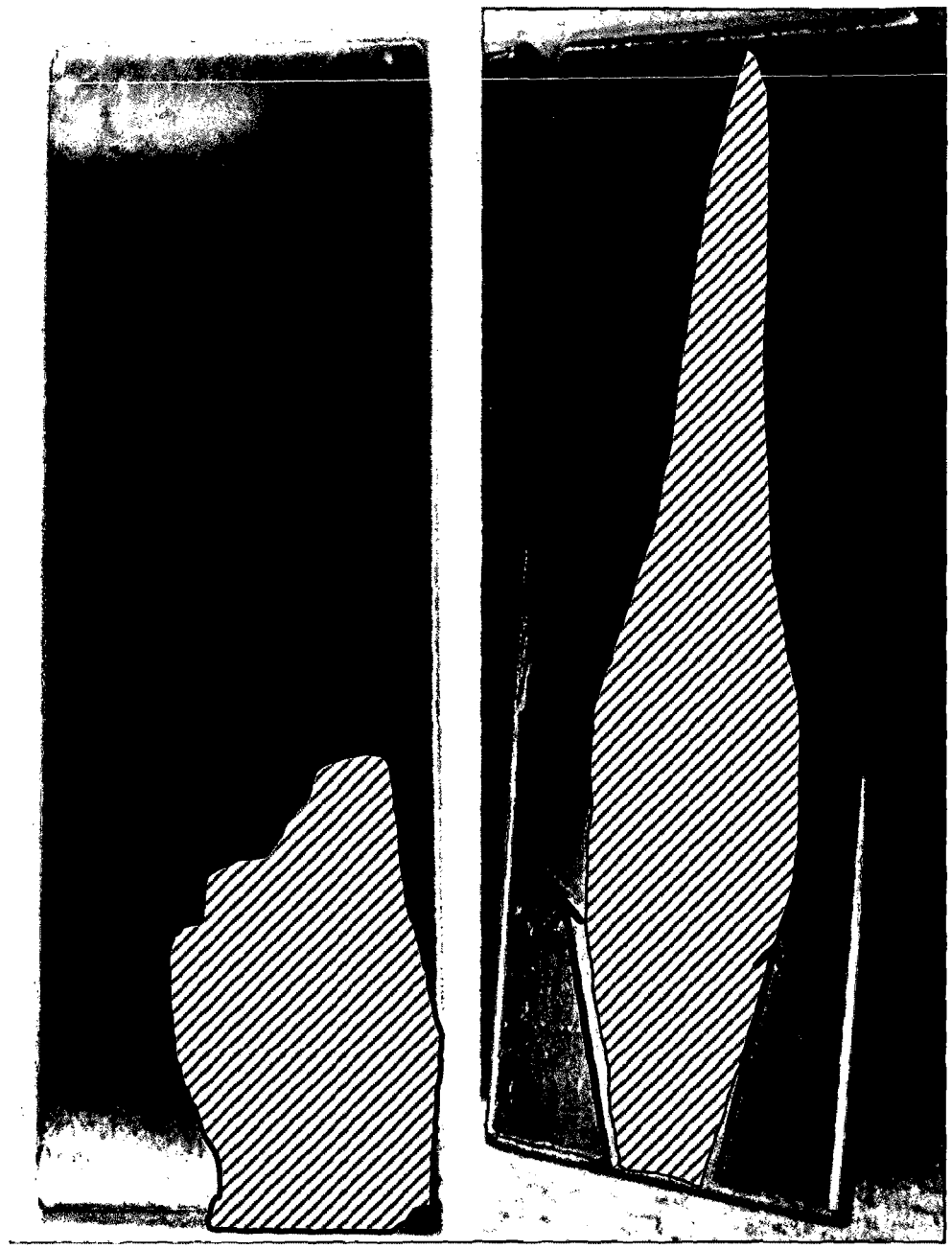
FIG. 6 depicts contamination effects of ion beams at the entrance of DMS electrodes.

FIG. 6 shows experimental results comparing contamination effects for a standard DMS configuration and a jet injector DMS configuration. In each case, a sample comprising undiluted Hank's Buffer solution was directly infused on the mass spectrometer at ~75 µL/min for approximately 15 hours. Hank's Buffer is a cell culturing media that has a very high salt content, and leaves a clear debris pattern on the DMS electrodes that correlates with the gas flow. In each case, these experiments were performed with an AB Sciex Turbo V™ ion source oriented orthogonally to the DMS inlet. The two electrodes shown in FIG. 6 are from a standard DMS cell configuration (top pane) and a jet injector DMS configuration (bottom pane). Referring first to the standard DMS cell, the bulk of debris has been outlined for easier visualization and is located on the lower half of the DMS entrance, consistent with the orthogonal nature of the spray. Given that this configuration uses a DMS cell sealed to the orifice to establish laminar flow conditions down the length of the cell, significant signal losses may be expected due a significant fraction of the ions entering in the lower velocity region close to the cell holder wall. Conversely, with the jet injector, the debris is roughly centered relative to the DMS electrodes, and form a pattern consistent with a gas jet. In this case, the ions enter the cell in the optimal location for transmission (i.e. on the axis of the cell).

A series of modified DMS holders were utilized to evaluate the effects on the incorporation of a jet injector electrode prior to a conventional DMS. A flat plate with a small aperture was braised onto the front of a ceramic DMS holder. The length of the DMS electrodes were 28 mm compared to 30 mm used in the conventional DMS which was used to minimize arcing effects. Various aperture sizes were varied in 0.25 mm increments from 0.5 mm to 3.5 mm for these experiments. The jet injector electrode shields the ions from the DC potentials applied to the DMS electrodes, and due to its sealing into the holder generates a gas beam or jet into the front of the DMS electrodes, minimizing time spent by the ions in the fringing field.

Figure 7:
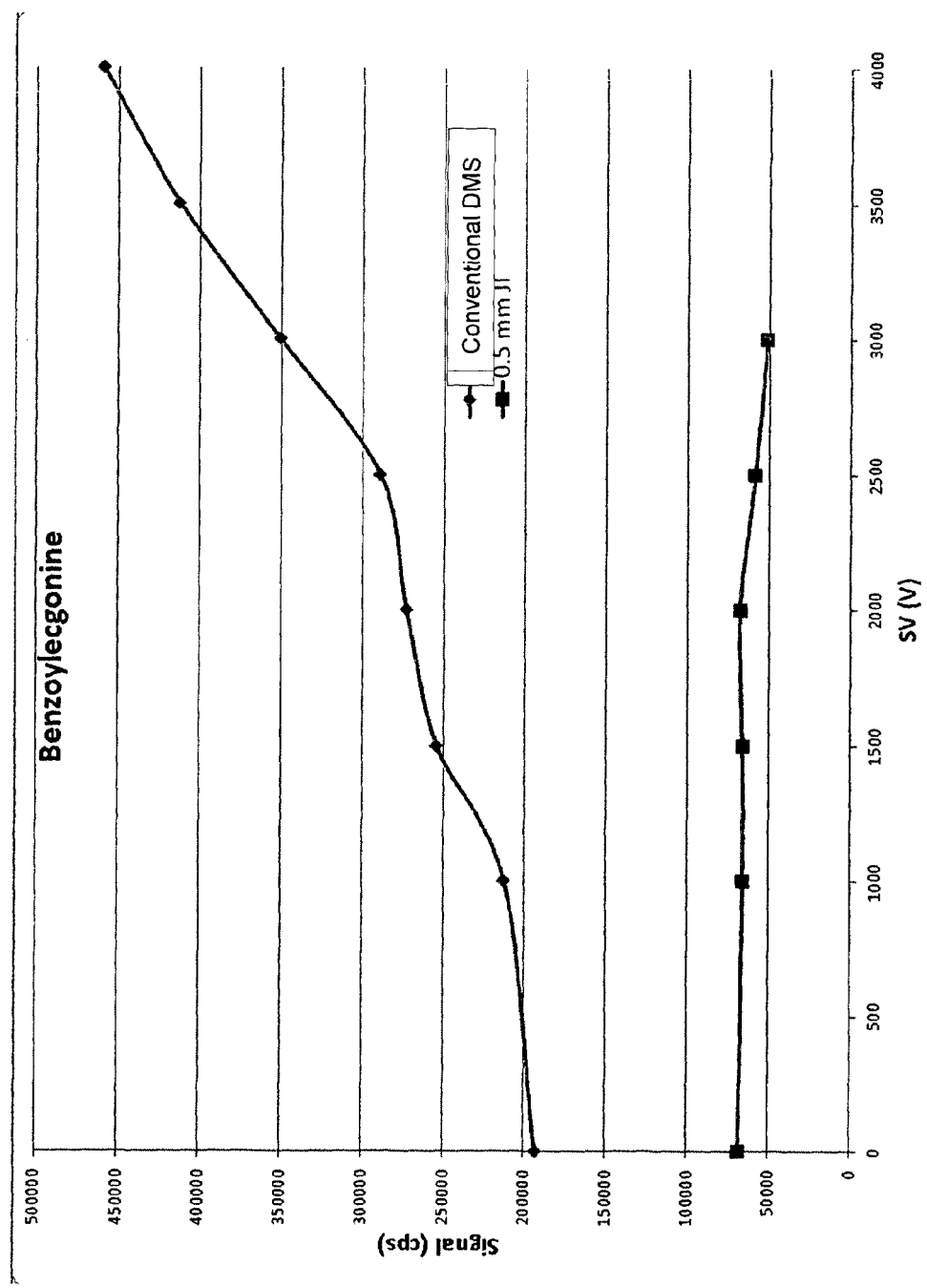
FIG. 7 depicts the effect of shielding on the fringing effects of the DMS on benzoylecgonine response, with a small non optimized 0.5 mm jet injector.

One example of the fringing field effects is depicted in FIG. 7 where a DMS configured with a 0.5 mm jet injector electrode was compared to a typical DMS system. This figure demonstrates the data acquired with increasing separation voltage (SV) for the compound benzoylecgonine. At a SV of zero, consistent with a DMS operating in transparent mode, the signal for the conventional DMS device (depicted in FIG. 1 or 2 at 193,043 cps was approximately only 2.8 times greater than what was observed with a DMS modified with the presence of a 0.5 mm jet injector at 68,377 cps, despite the inlet cross sectional area being approximately 20.4 times smaller in the modified system.

Increasing the SV gives a signal boost of slightly greater than two times for this compound with the conventional DMS configuration, helping to restore the signal lost in the inlet fringing field. Conversely, with the jet injector electrode, the modified DMS behaves as theoretically predicted (Krylov E V., "Comparison of the Planar and Coaxial Field Asymmetrical Waveform Ion Mobility Spectrometer (FAIMS)", Int. J. Mass Spectrom., 2003, 225, 39-51.), where no increase in signal is seen with increasing SV, due to the shielding effect due to the presence of the jet forming electrodes. These results demonstrate that a jet injector electrode can provide a method of efficiently shielding ions from detrimental fringing fields, whether they are caused by the presence of upstream lens elements maintained at higher potentials, such as a curtain plate, or DC offsets between DMS electrodes (i.e. CoV). This demonstrates two advantages of a jet injector electrode inlet for DMS devices; the electrode can shield the DMS cell from fringing effects that can occur between a DMS inlet and an upstream electrode maintained at high potential, and the combined shielding and gas beam/jet established into the front of a DMS can provide more efficient transport of ions.

Figure 8:
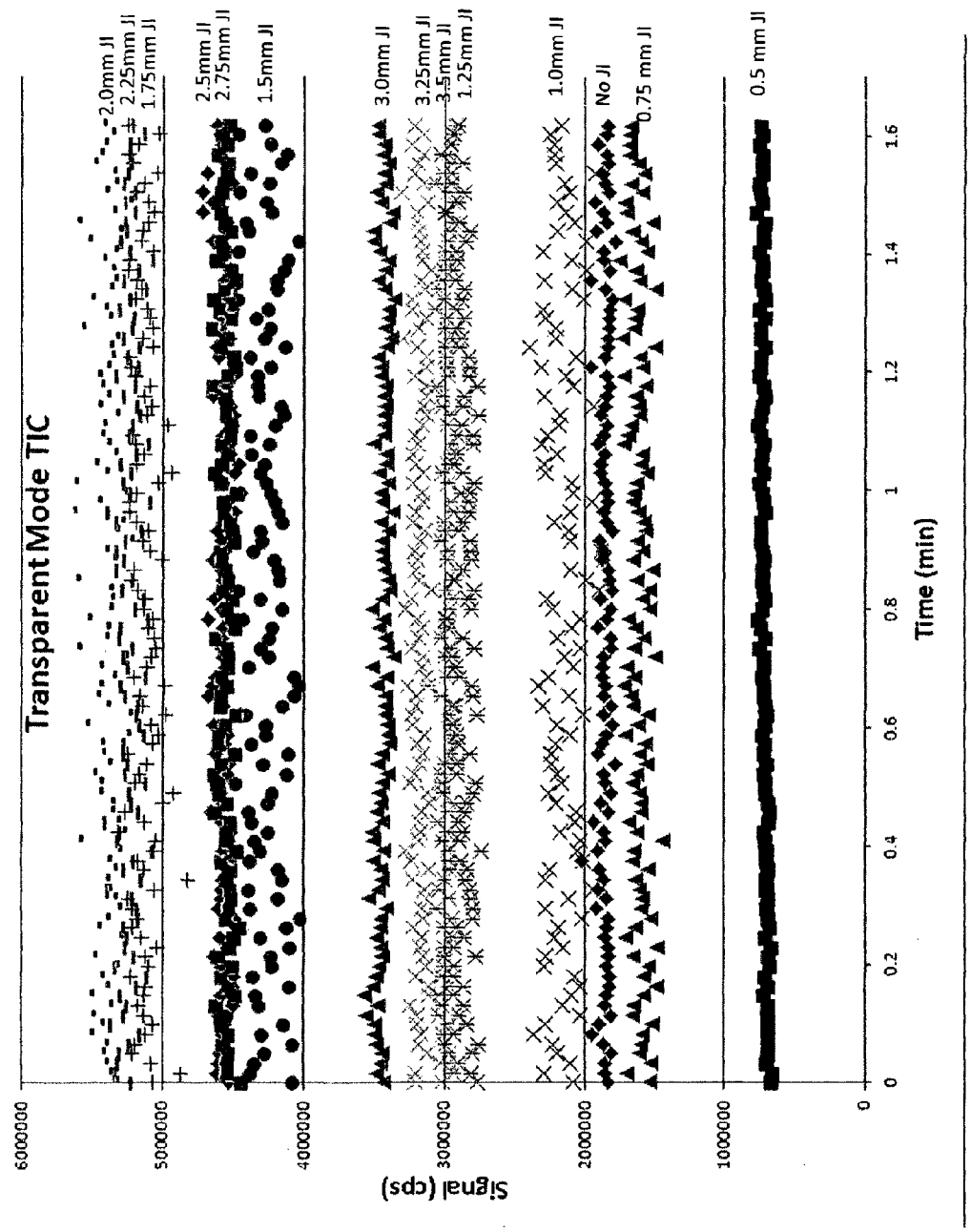
FIG. 8 depicts the effect on peak width of different jet injection configurations.

FIG. 8 shows a comparison of the transparent mode total ion current (TIC) observed for a mixture of 14 compounds using a series of different DMS configurations with an analytical gap width of 1 mm, including a conventional DMS device, and 13 different jet injector configurations of varying orifice size.

Figure 9:
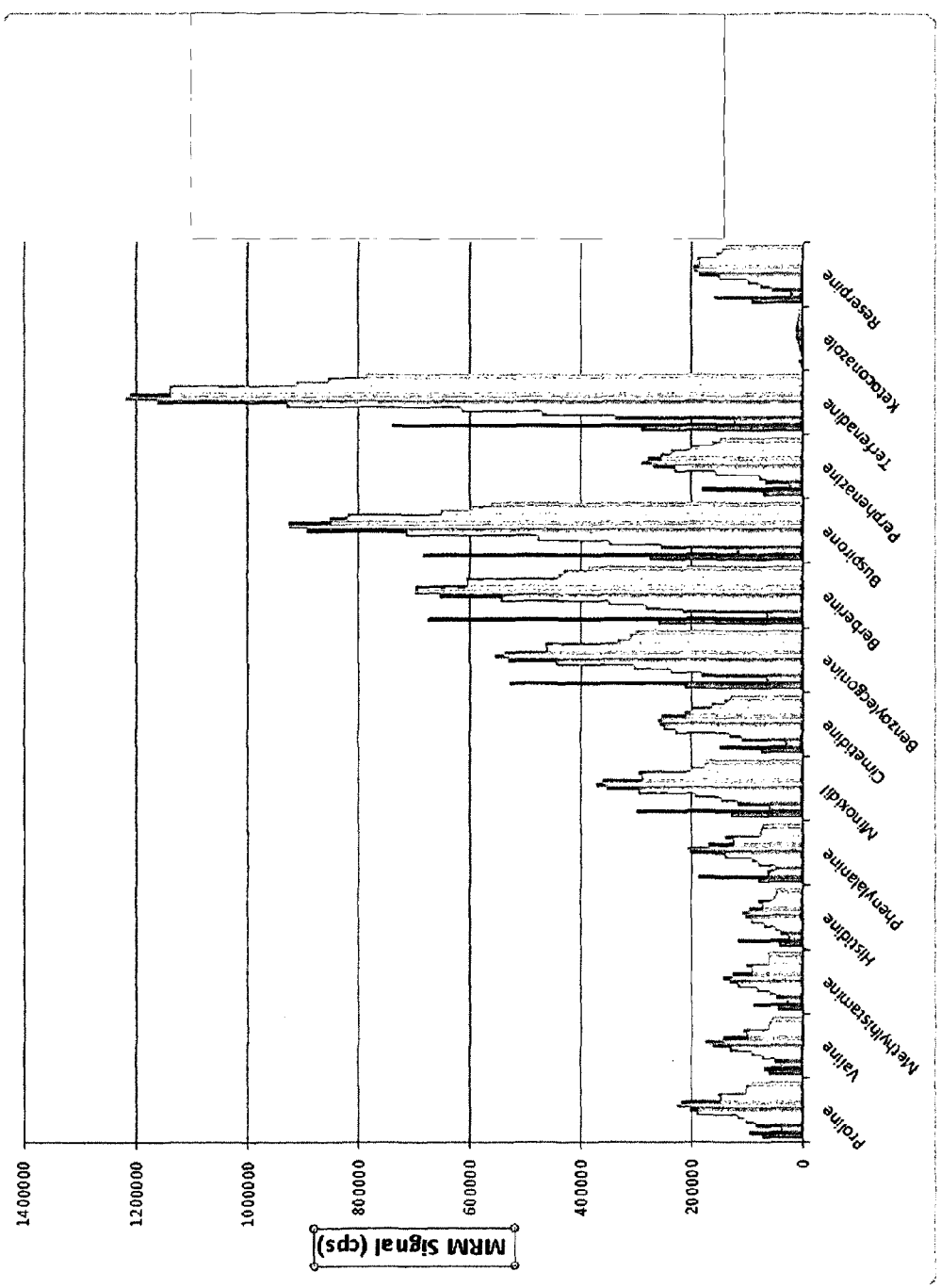
FIG. 9 shows MRM signal for several compounds with a conventional DMS device and various jet mode injectors.

Referring to FIG. 8, the diamonds with signal count rates of just under 2,000,000 cps show the TIC data acquired with a conventional DMS device in transparent mode. It is seen that with the use of a jet injector electrode, that increasing the orifice size of the jet injector electrode from 0.5 mm to about 2.25 mm is beneficial in terms of signal, displaying a maximum increase over the conventional DMS on the order of about 3× for transparent mode. Further increases in the diameter of the jet injector electrode lead to reduced signal, however, the transparent mode TIC with the maximum jet injector electrode orifice of 3.5 mm displayed about 1.6 times higher intensity than the conventional DMS device, without jet injector. These data are plotted separately for each of the mixture components in FIG. 9 which shows plots of the measured MRM intensity for each component of the mixture under various jet injector electrodes orifice sizes and for a conventional DMS. For each compound, a series of bar graphs is displayed. From left to right, each of the bars corresponds to 1) Conventional DMS operating in transparent mode (No separation voltage or compensation voltage), 2) Conventional DMS operating with separation field (~115.5 Td), 3) 0.5 mm Jet Injector electrode, 4) 0.75 mm Jet Injector electrode, 5) 1.0 mm Jet Injector electrode, 6) 1.2 mm Jet Injector electrode, 7) 1.5 mm Jet Injector electrode, 8) 1.778 mm Jet Injector electrode, 9) 2.0 mm Jet Injector electrode, 10) 2.25 mm Jet Injector electrode, 11) 2.5 mm Jet Injector electrode, 12) 2.75 mm Jet Injector electrode, 13) 3.0 mm Jet Injector electrode, 14) 3.25 mm Jet Injector electrode, 15) 3.5 mm Jet Injector electrode. No separation voltage was applied to any of these electrodes.

A majority of the jet injector data points display greater signal counts than the conventional DMS system. In addition, this demonstrates that the jet injector inlet utilized for the DMS can provide increased ion transmission.

Figure 10:
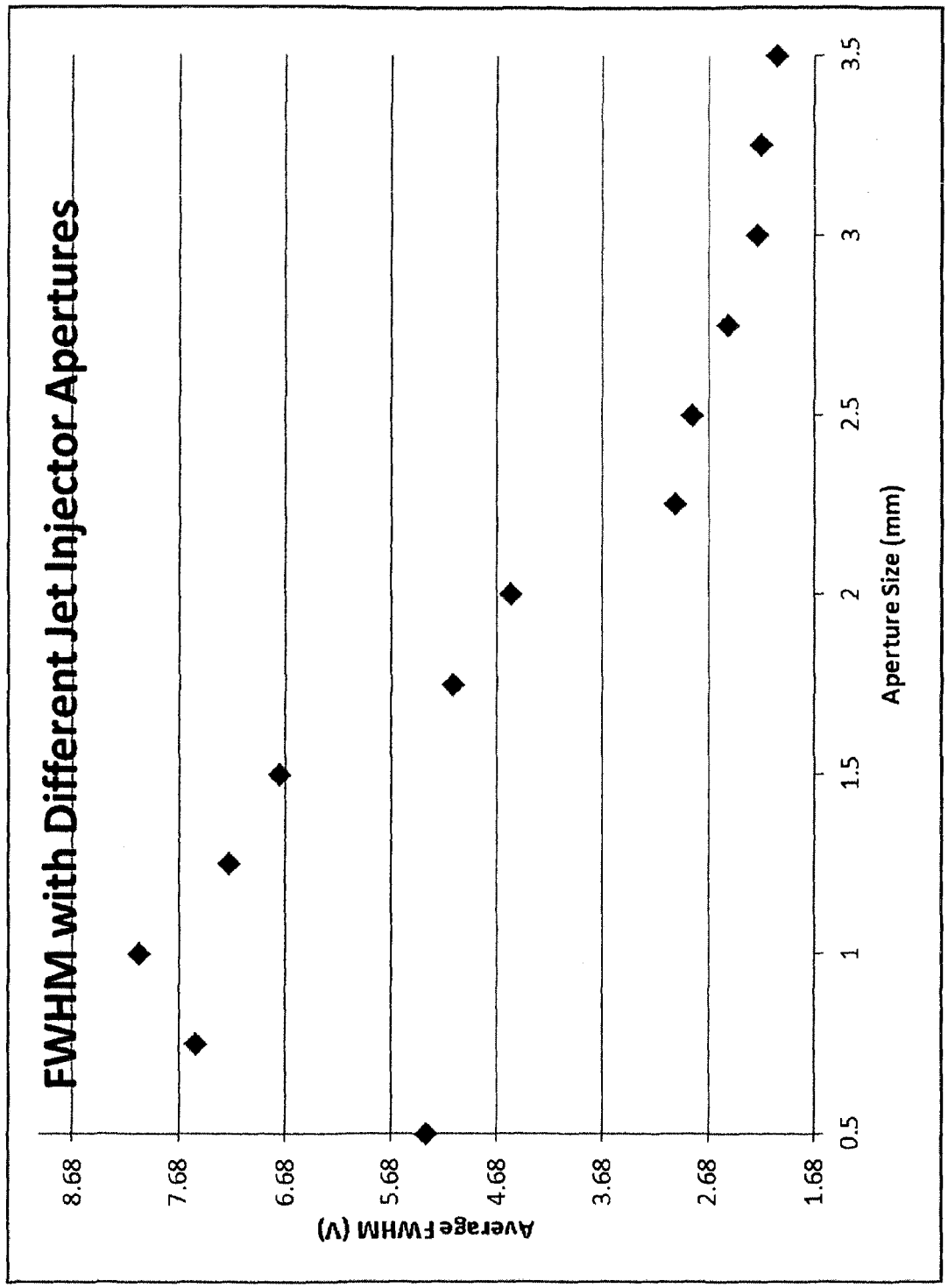
FIG. 10 depicts average Full Width at Half Maximum (FWHM) plots for the compound mixture at varying injector device aperture diameters.

DMS peak width effects were also evaluated with the jet injector electrode modified DMS devices as shown in FIG. 10. The average observed peak width for the fourteen compound mixture is plotted with the various jet injector electrode orifice size configurations. The value with an unmodified DMS is the origin of the y axis (i.e., 1.68 V Full Width at Half Maximum (FWHM)). Given the slightly shorter DMS electrode length (28 mm vs. 30 mm), a FWHM increase of about 0.2 V would be expected. As shown in FIG. 10, the average FWHM with the 0.5 mm jet injector was 5.34 V, demonstrating a substantial resolution loss relative to an unmodified device. The peaks broadened further as the jet injector aperture was increased to match the DMS gap height (1 mm). At this point the intensity of the modified DMS response became close to the intensity of a conventional DMS. However, further increases in the jet aperture diameter lead to narrowing of the DMS peak widths, and simultaneously increasing signal, presumably due to a reduced gas jet distribution into the front of the DMS and a smaller fraction of the beam actually impacting the inlet slot. In fact, when the jet injector aperture was increased to 3.5 mm, the observed FWHM was very close to the expected value for the unmodified device despite the fact that the electrodes were 2 mm shorter.

The results present in FIG. 10 demonstrate an additional potential advantage for a jet injector electrode inlet for DMS. By using an electrode that can vary the size of the aperture, finite control can be maintained between resolution and sensitivity in an analogous fashion to what is achieved for example in U.S. Pat. No. 8,084,736, herein incorporated by reference, without requiring the need to provide additional gas flows (such as throttle gases) or suction/vacuum. The variation of the size of the aperture can be achieved for example by physically substituting differing jet injector electrodes or by using an iris diaphragm control system. Iris-diaphragm flow control systems are similar in concept to the aperture system in a lens on a camera that controls the amount of light entering the camera. The iris system is generally comprised of three or more fingers arranged circumferentially around the flow path that can be moved into the flow area to obstruct the flow of gas. Generally the more fingers that are utilized, the more circular the aperture that is formed at the expense of increased complexitiy.

Figure 11:
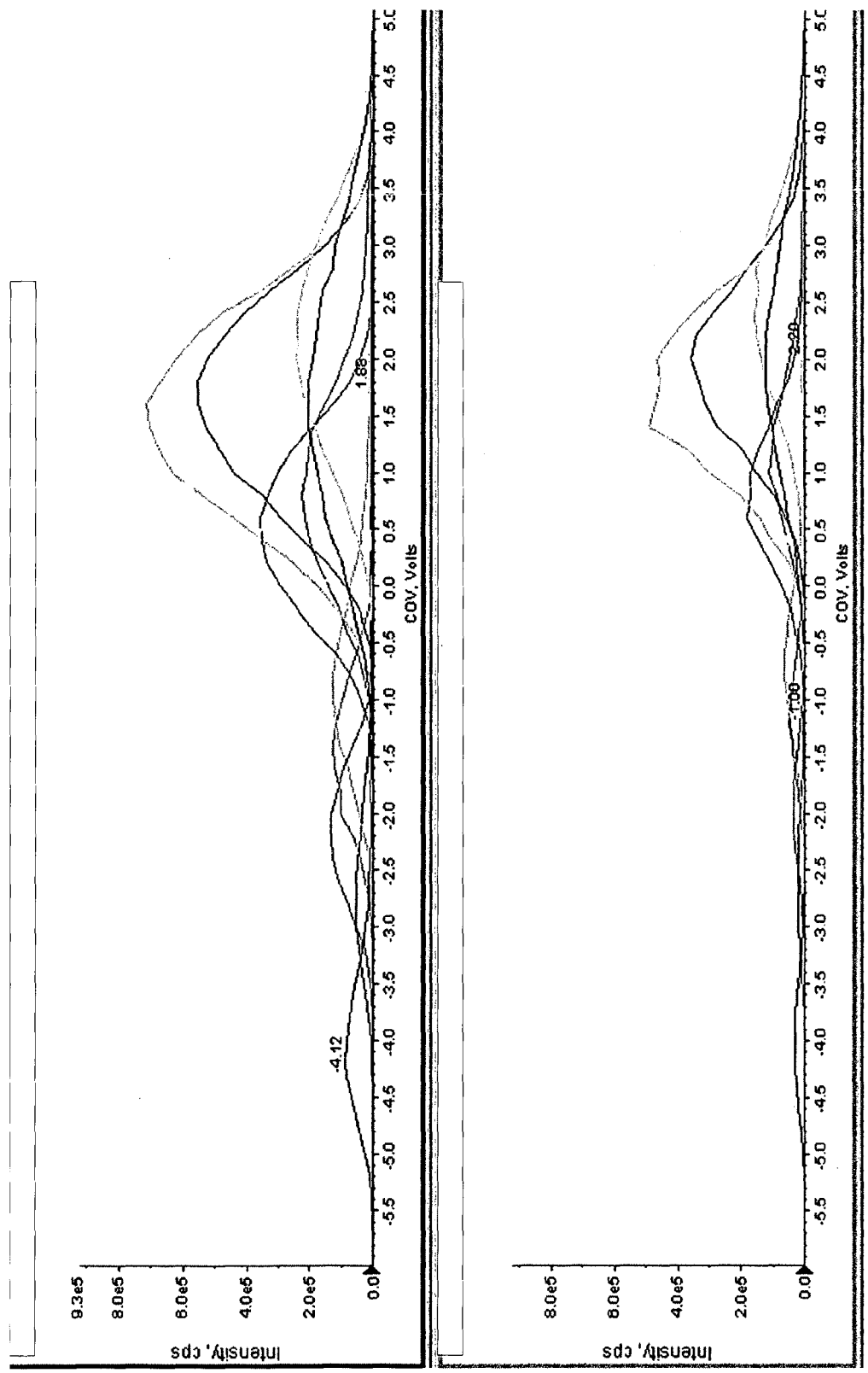
FIG. 11 depicts ionogram intensities of a 3.5 mm (optimized) injector aperture compared to a conventional DMS device
Figure 12:
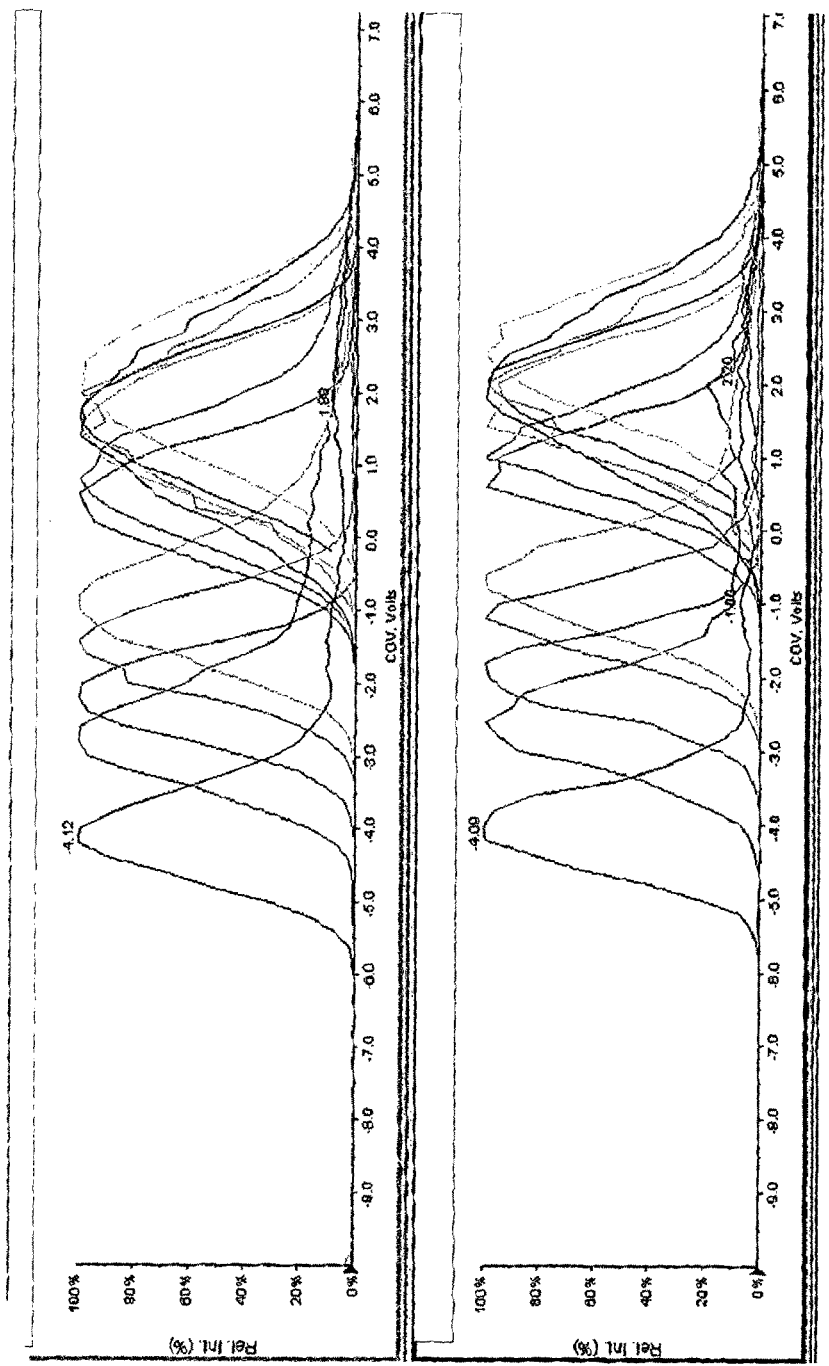

As demonstrated in FIGS. 11 and 12, the observed resolution with the 3.5 mm jet injector device (top trace) was similar to what was observed with an unmodified DMS device (lower trace) with separation field ~115.5 Td applied. FIG. 11 shows a comparison of ionograms for the fourteen compound mixture with these two devices where the y-axis has been scaled similarly to demonstrate the signal gain observed with the jet injector (top pane) versus the standard DMS (bottom pane). FIG. 12 presents the same information as in FIG. 11 except that the data has been normalized to demonstrate that similar resolution is observed with the two mobility cells.

Figure 13:
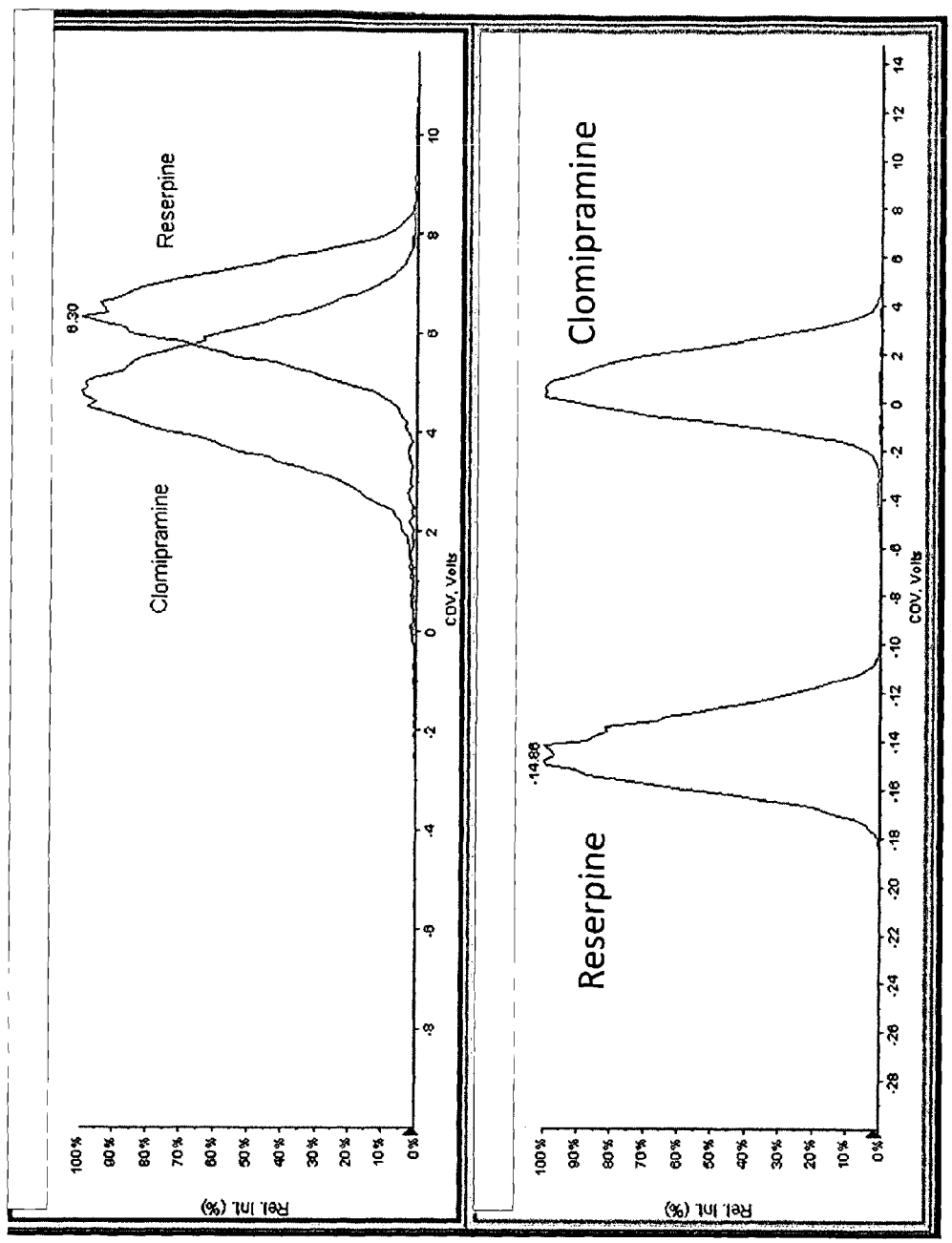
FIG. 13 depicts ionograms for the compounds reserpine and clomipramine analyzed using a jet injector electrode with and without chemical modifiers.

The within described modifications can also be utilized in DMS systems that use chemical modifiers to increase resolution. FIG. 13 shows two ionogram plots of a mixture containing clomipramine and reserpine using a jet injector electrode in accordance with the present teachings. The upper ionogram plot was conducted with no use of chemical modifier whereas the lower ionogram was obtained using 1.5% isopropanol chemical modifier demonstrating that the jet injector electrode has little impact on the usefulness of chemical modifiers utilized in a DMS system, which shows that DMS with jet injectors function with chemical modifiers.

Figure 14:
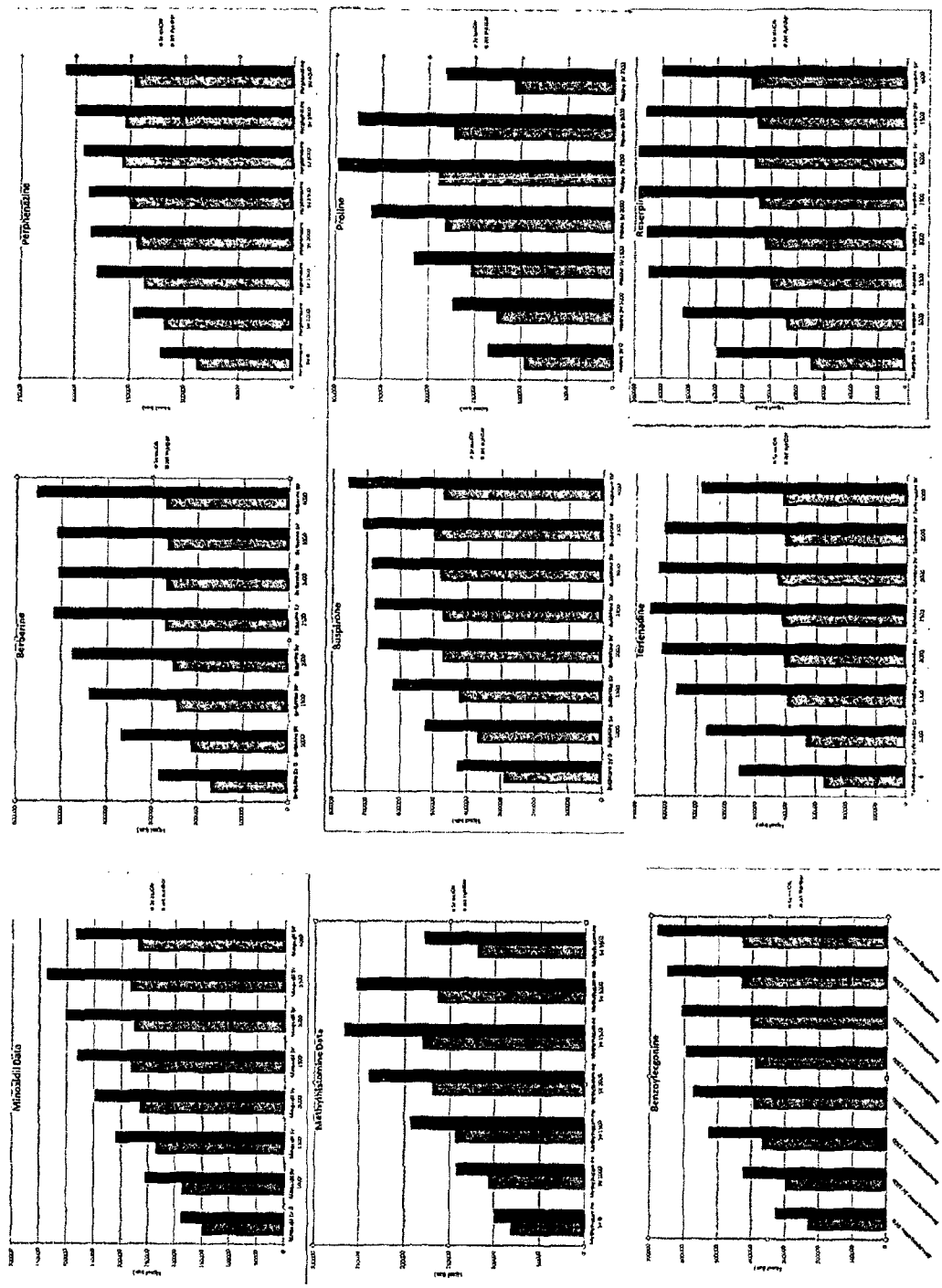
FIG. 14 depicts a series of plots of nine compounds and the intensity traces at various Separation Voltage values with a conventional DMS (left bar) and one modified in accordance with the present teachings (right bar)

A series of experiments were conducted to verify transmission characteristics for a multi-compound mixture with various SV settings ranging from 0 V to 4000 V (~132 Td). FIG. 14 shows the transmission intensities for minoxidil, berberine, perphenazine, methylhistamine, buspirone, proline, benzoylecgonine, terfenadine and reserpine at various separation voltages. The first bar at each separation voltage is for a conventional DMS configuration whereas the second bar is for a DMS modified with 3.5 mm aperture jet injector electrode. The gains observed for the jet injector ranged from approximately 1.38× to 2.00× when compared to the unmodified DMS.

The improvements in performance by the use of the within teachings are also observed when utilized in high flow rate conditions. Various compounds were analyzed by flow injection analysis (FIA) with a nebulizer assisted electrospray ion source at a flow rate of 500 uL/min with source heaters optimized to 750° C. for each of the compounds. A heat exchanger was incorporated into the curtain plate to increase the temperature of the curtain gas/transport gas to ~150° C. The data are summarized in Table 1 for the average of five injections with each configuration. Comparing first the transmission with the standard non modified DMS cell and a standard mass spectrometer instrument, there was a sensitivity reduction of 4.5-9.7× depending upon the compound. These losses were reduced on average by about a factor of two when the jet injector electrode set was used instead.

TABLE 1

FIA results for Standard Mass Spectrometer with no DMS, Standard Mass Spectrometer with Standard DMS and Standard Mass Spectrometer with Jet Injector DMS.

| Sample | Mass Spec-No DMS (No DMS) | Mass Spec-Conventional DMS (DMS) | Mass Spec-JI DMS (JI DMS) | (No DMS)/ (DMS) | (No DMS)/ (JI DMS) | (JI DMS)/ (DMS) |
|---|---|---|---|---|---|---|
| Reserpine | 913,320 | 189,120 | 401,250 | 4.83 | 2.28 | 2.12 |
| Minoxidil | 2,557,400 | 294,640 | 622,360 | 8.68 | 4.11 | 2.11 |
| Proline | 2,222,200 | 309,260 | 742,960 | 7.19 | 2.99 | 2.40 |
| 5-FU | 311,900 | 32,204 | 59,838 | 9.69 | 5.21 | 1.86 |
| Taurocholic Acid | 835,120 | 185,520 | 325,880 | 4.50 | 2.56 | 1.76 |
| Range | | | | 4.5-9.7 | 2.3-5.2 | 1.8-2.4 |

Figure 15:
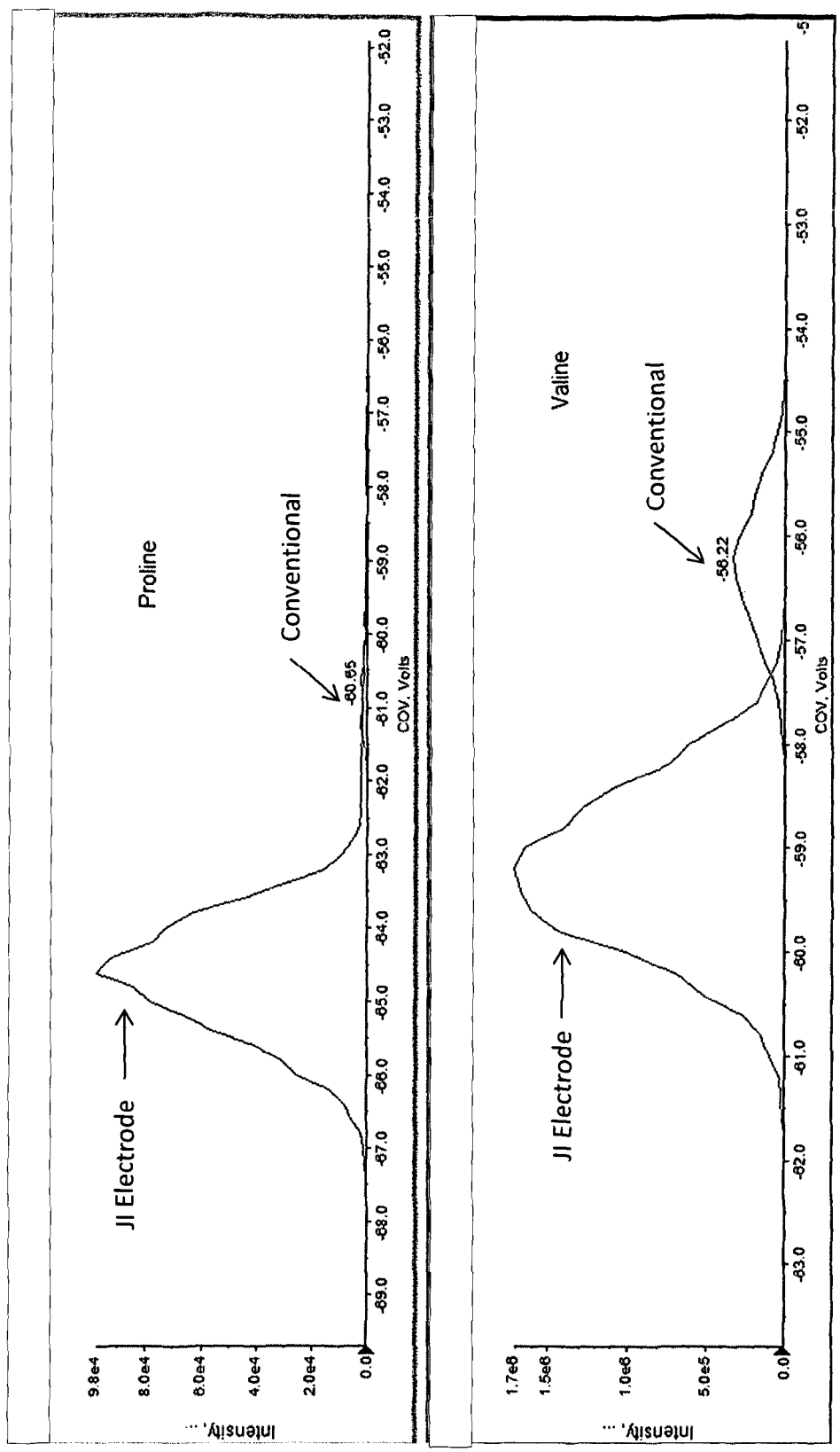
FIG. 15 depicts ionograms of proline and valine analytes (high coefficients of mobility) using a conventional DMS and one in accordance with the present teachings.

The within teachings have also been found to have significant benefits when used with compounds exhibiting dramatic alpha behavior. Compounds with extremely steep alpha curves can require very high compensation voltage values to transmit through the DMS. These compounds will be most prone to inlet fringing field issues, particularly if they have large low field mobility. Examples of these types of compounds are proline and valine ions when utilized in the presence of an isopropanol modifier. FIG. 15 shows an example of ionograms acquired for proline (top) and valine (bottom) with the jet injector electrode utilized with a jet injector DMS and a standard DMS cell not utilizing the jet electrode with identical settings (SV=3500 V, DMO=60 V, curtain gas=20 psi). Under these conditions, where the CoV value is quite large, the benefits of the jet injector electrode become substantial.

While the teachings described herein provide an alternative to the methodology of increasing resolution described in U.S. Pat. No. 8,084,736, herein incorporated by reference, the two methodologies are not mutually exclusive and can be used together in a synergistic way to improve resolution.

Figure 16:
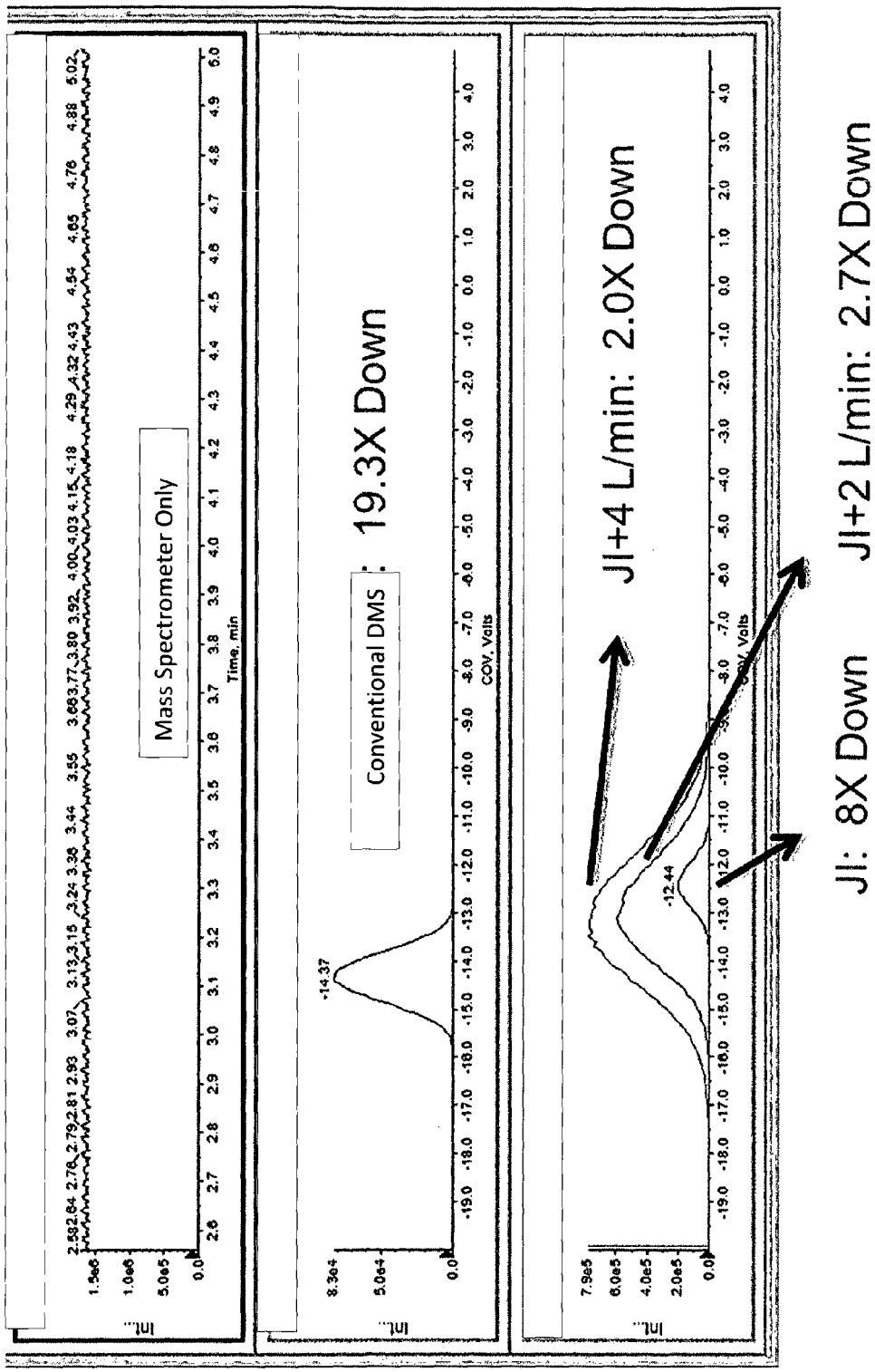
FIG. 16 depicts data for triazole using various conditions and apparatus

Triazole is a very low mass compound that has poor transmission characteristics through a conventional DMS device, and this is believed to be due in part to the presence of the inlet fringing fields effects of a DMS device described herein and the relatively high mobility characteristics exhibited by the ion. A sample of triazole was infused at 10 uL/min, and the source heaters were optimized to 300° C. The top pane of FIG. 16 shows infusion data acquired with a standard mass spectrometer system for this compound, demonstrating approximately 1.6×10⁶ cps signal intensity. The middle pane of FIG. 16 shows an ionogram generated with amass spectrometer system outfitted with a conventional DMS cell operating under optimized conditions, which demonstrates an almost 20× signal reduction compared to the standard instrument with no DMS cell. The bottom pane of FIG. 16 shows ionograms taken with a mass spectrometer system outfitted with a conventional DMS cell that had a jet injector electrode installed under various conditions. The trace in the bottom pane with no additional gas flow demonstrates approximately 2.4 times improvement over the standard conventional DMS cell device, but still approximately 8 times lower sensitivity than the no DMS instrument. The other two traces show data acquired using the jet injector electrode analyzed with the gas flow through the device augmented by 2 L/min and 4 L/min. The signal intensity with the jet injector electrode and the 4 L/min augmented gas flow was within about a factor of 2 of the standard instrument. This represents almost a 10-fold gain over the data acquired using the non-modified DMS device.

Figure 17:
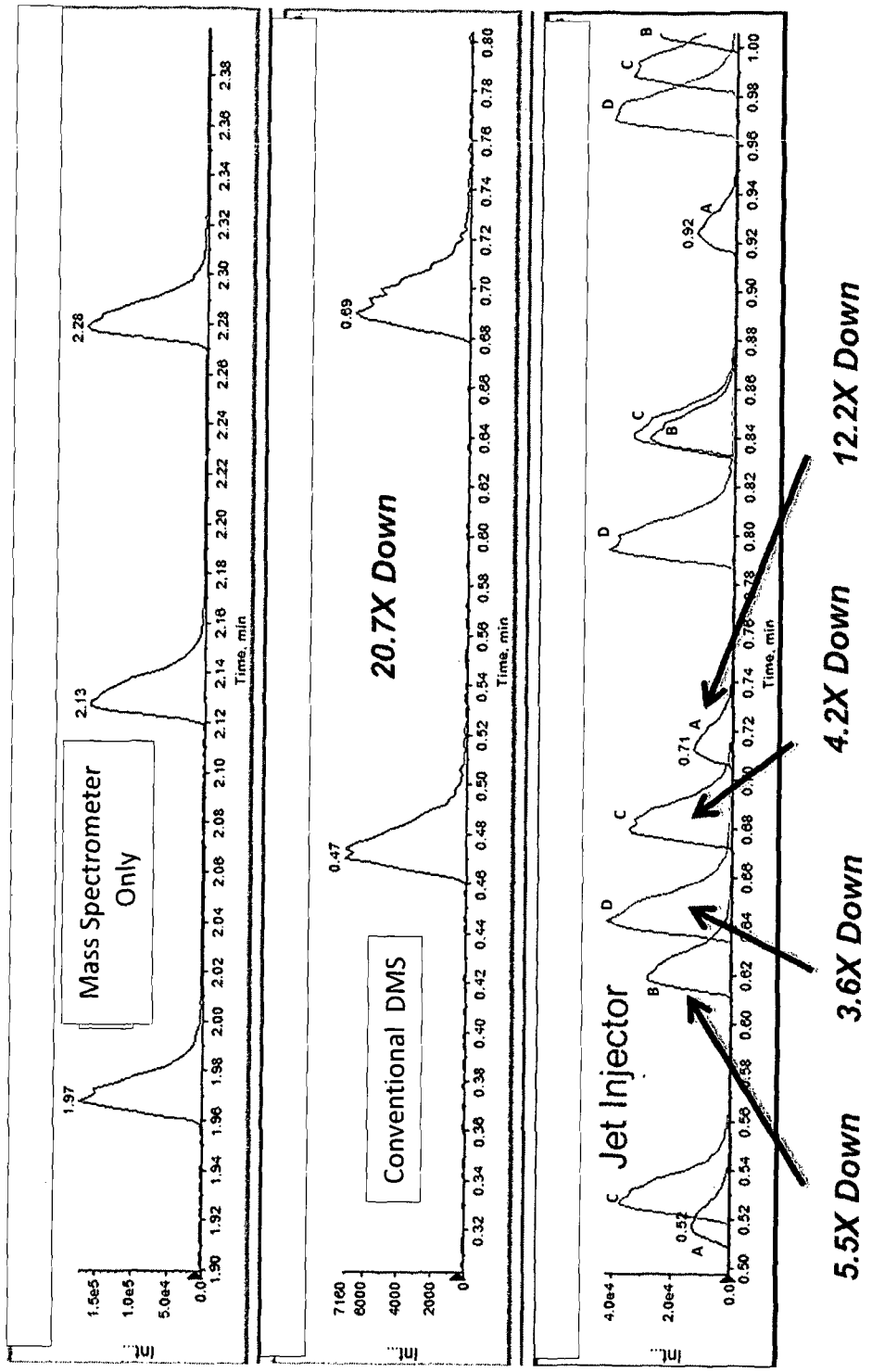
FIG. 17 depicts ionograms for triazole using various conditions and apparatus at higher sample flow rates

FIG. 17 shows a similar experiment performed using the triazole compound with FIA at 500 uL/min. The peak area for the triazole compound was 166,927 counts with the standard mass spectrometer device (top pane of FIG. 17). The middle pane of FIG. 17 shows results after installation of a conventional DMS cell, demonstrating ~21× reduction in sensitivity as a result of the DMS cell. The bottom pane shows results with the jet injector and various transport gas flow rates. The data for the standard jet injector is shown in the (A) trace, where the signal for the triazole compound improved by ~2× compared to a conventional DMS cell. The (B), (C), and (D) ionograms demonstrate the data acquired with the gas flow through the jet injector augmented by 2 L/min, 4 L/min, and 6 L/min, respectively. The total gain in signal over the standard DMS cell was roughly 6× when using up to 6 L/min of gas flow augmentation.

The combination of jet injector DMS cell and augmented gas flow provides benefits for other compounds as well at high flows. Table 2 shows data acquired for 5 different compounds for flow injection analysis at 500 uL/min. These compounds exhibited smaller losses with the standard DMS cell than the previously described triazole compound, demonstrating a range of 4.5-9.7× down relative to the standard 5500. The jet injector cell improved transmission by about a factor of 2, however augmenting the gas flow through the jet injector cell further improved performance by about another factor of 2. The signal with the jet injector and 4 L/min ranged from 1.3-2.0× down relative to the standard instrument, demonstrating substantial improvement over the standard jet injector cell.

TABLE 2

Relative peak areas for 5 different compounds using a number of different analysis configurations.

| Sample | Std. MS/ Std. DMS | Std. MS/ DMS with Jet Injector | Std. MS/ DMS with Jet Injector + 2 L/min | Std. MS/ DMS with Jet Injector + 4 L/min |
|---|---|---|---|---|
| Reserpine | 4.8 | 2.3 | 1.5 | 1.3 |
| Minoxidil | 8.7 | 4.1 | 2.3 | 2.0 |
| Proline | 7.2 | 3.0 | 1.5 | 1.4 |
| 5-FU | 9.7 | 5.2 | 1.9 | 1.6 |
| Taurocholic Acid | 4.5 | 2.6 | 1.4 | 1.3 |
| RANGE | 4.5-9.7 | 2.3-5.2 | 1.4-2.3 | 1.3-2.0 |

It should be understood that the within description of numerous embodiments has been presented for purposes of illustration and description. It is not exhaustive and is not intended to limit the claimed inventions to the precise forms disclosed. Modifications and variations are possible in light of the above description or may be acquired from practicing the invention. For example, while embodiments have been specifically disclosed wherein the jet injector electrode is an electrode, it would be appreciated that the jet injector properties and the reduction of time that ions spend within the fringing fields would also be present when an insulator material is used in place of the jet injector electrode, but still otherwise contains an aperture and is sealingly engaged to the parallel plate electrode. The claims and their equivalents define the scope of the invention. Additionally the benefits of the jet injector could also be realized for a system that does not include a low pressure region after the DMS cell. In this case there would be no suction from behind the cell to pull transport gas through the analyzer. Conversely, the pressure in the region prior to the jet injector aperture could be increased to cause the transport gas to flow through the DMS cell. In this case, the transport gas flow would be "pushed" from the front rather than "pulled" from the back.

The invention claimed is:

1. A differential mobility apparatus comprising:
   a housing having an entrance and an exit;
   at least two parallel plate electrodes disposed within said housing separated from one another by a fixed distance, the volume between the two electrodes defining an ion path through which ions flow from the entrance to the exit, the ion path having a cross-sectional area normal to the direction of ion flow;
   a voltage source for providing RF and DC voltages to at least one of the parallel plate electrodes to generate an electric field, the electric field for passing though selected ions species based on mobility characteristics;
   a drift gas supply for supplying a gas that flows through the entrance to the exit; and
   at least one entrance electrode plate sealingly engaged to the entrance, and electrically separated from the parallel plate electrodes, the at least one entrance electrode plate having an aperture for allowing the traversal of ions and the gas into the housing;
   wherein the cross-sectional area of the aperture is less than the cross-sectional area of the ion path.

2. The differential mobility apparatus of claim 1 wherein the apparatus operates in transparent mode.

3. The differential mobility apparatus of claim 1 wherein the at least one entrance electrode plate is removable.

4. The differential mobility apparatus of claim 1 wherein the aperture is contained within an iris diaphragm and is adjustable to vary the flow of gas through the entrance.

5. The differential mobility apparatus of claim 1 wherein the at least one entrance electrode plate is electrically separated from the parallel plate electrodes and wherein a controller and generator are connected to the at least one entrance electrode plate for applying an RF focusing potential and/or a DC potential.

6. The differential mobility apparatus of claim 1 further comprising a vacuum source positioned downstream from said parallel plate electrodes.

7. The differential mobility apparatus of claim 1 wherein the housing is surrounded by a curtain plate that defines a curtain chamber and the curtain chamber is in fluid communication with a curtain gas supply that provides a curtain gas to the curtain chamber wherein the curtain gas in the curtain chamber becomes the drift gas supply, the curtain chamber having at least one aperture which allows ions to flow there through.

8. The differential mobility apparatus of claim 1 wherein the aperture is either circular or slit shaped.

9. The differential mobility apparatus of claim 1 wherein two electrode plates are sealingly engaged to the entrance and each of the two electrode plates are electrically insulated from the parallel plate electrodes and each of the two electrode plates is electrically insulated from each other, each of the two electrode plates being connected to an RF source and controller for generating an RF focusing field.

10. The apparatus of claim 1 wherein two entrance electrode plates are sealingly engaged to the entrance, the two entrance electrode plates being electrically insulated from each other, the first of the entrance electrode plates defining a first cut out portion and the second of the entrance electrode plates defining a second cut out portion, the first and second cut out portions co-operating to form the aperture, and optionally wherein an RF focusing potential is applied from the first entrance electrode plate to the second entrance electrode plate.

11. A method of analyzing ions in a differential mobility device, the device having two parallel olate electrodes that generate an electric field, the method comprising:
   introducing ions into a drift gas and directing said drift gas towards an inlet of the differential mobility device;
   accelerating the drift gas as it enters the differential mobility device and decelerating the drift gas once the drift gas has entered the differential mobility device;
   performing a differential mobility separation on the ions using the differential mobility device; and
   detecting the ions;
   wherein the accelerating of the drift gas comprises passing the drift gas through an aperture that is defined within one or more electrode plates that are sealingly engaged to the face of the parallel plates and the decelerating of the drift gas is performed by the expansion of the drift gas upon exiling the aperture, wherein the cross section of the aperture is less than the cross section of the inlet of the differential mobility device.

12. The method of claim 11 wherein the accelerating of the drift gas also comprises applying suction downstream from the two parallel plate electrodes, the suction being provided by a vacuum source.

13. The method of claim 11 wherein an RF focusing potential is applied to the one of more electrode plates for focusing of the ions.

14. A method of analyzing ions in a differential mobility device, the device having two parallel plate electrodes that generate an electric field, the method comprising:
   introducing ions into a drift gas and directing said drift gas towards an inlet of the differential mobility device;
   accelerating the drift gas as it enters the differential mobility device and decelerating the drift gas once the drift gas has entered the differential mobility device;
   performing a differential mobility separation on the ions using the differential mobility device; and
   detecting the ions;
   wherein the differential mobility device is surrounded by a curtain plate which defines a curtain chamber and the curtain chamber is in fluid communication with a curtain gas supply that provides a curtain gas to the curtain chamber wherein the curtain gas becomes the drift gas that flows into the differential mobility device, and the curtain plate has at least one aperture that allows ions to flow there through.

15. A differential mobility filler apparatus system comprising:
- an ionization source for generating ions;
- a curtain chamber defined by at least one curtain plate, the curtain plate containing a curtain plate aperture through which the ions flow;
- a curtain gas supply in fluid communication with the curtain chamber;
- a housing disposed within the curtain chamber, the housing having an opening and an exit, the volume between the opening and exit defining an ion path, the ion path being generally in line with the curtain plate aperture and the opening being in fluid communication with the curtain chamber;
- at least two parallel plate electrodes disposed within the housing and being oriented opposite and separated by a fixed distance from one another on either side of the ion path;
- a voltage source and controller for providing RF and DC voltages to at least one of the parallel plate electrodes to generate an electric field, the electrical field for passing though selected portions of ions based on mobility characteristics;
- at least one entrance electrode plate sealingly engaged to the opening, and electrically separated from the parallel plate electrodes, the at least one entrance electrode plate having an aperture for allowing the traversal of ions and the gas into the housing;
- wherein the cross-sectional area of the aperture is less than the cross-sectional area of the ion path.

16. The differential mobility apparatus of claim 15 wherein the entrance electrode plate comprises an iris diaphragm, the iris diaphragm defining the aperture and being adjustable to vary the flow of gas through the opening.

17. The apparatus of claim 15 wherein the cross sectional area of the ion path is defined as the distance between the parallel plate electrodes times the width of the parallel plate electrodes.

18. The apparatus of claim 15 wherein an RF controller and generator is connected to the entrance electrode plate for applying an RF focusing potential.

19. The apparatus of claim 15 further comprising a vacuum source connected downstream from the two parallel plate electrodes, said vacuum source for accelerating curtain gas flow into and through the housing.

* * * * *